(12) United States Patent
Yamanaka

(10) Patent No.: US 10,085,693 B2
(45) Date of Patent: Oct. 2, 2018

(54) MEASURING DEVICE

(71) Applicant: Sharp Life Science Corporation, Kobe, Hyogo (JP)

(72) Inventor: Mikihiro Yamanaka, Osaka (JP)

(73) Assignee: SHARP LIFE SCIENCE CORPORATION, Kobe, Hyogo (JP)

( * ) Notice: Subject to any disclaimer, the term of this patent is extended or adjusted under 35 U.S.C. 154(b) by 463 days.

(21) Appl. No.: 14/774,307

(22) PCT Filed: Dec. 19, 2014

(86) PCT No.: PCT/JP2014/083758
§ 371 (c)(1),
(2) Date: Sep. 10, 2015

(87) PCT Pub. No.: WO2015/125396
PCT Pub. Date: Aug. 27, 2015

(65) Prior Publication Data
US 2016/0022214 A1   Jan. 28, 2016

(30) Foreign Application Priority Data
Feb. 20, 2014   (JP) ................................. 2014-031072

(51) Int. Cl.
*A61B 5/02*   (2006.01)
*A61B 5/00*   (2006.01)
(Continued)

(52) U.S. Cl.
CPC .......... *A61B 5/6843* (2013.01); *A61B 5/1455* (2013.01); *A61B 5/14546* (2013.01); *A61B 5/6826* (2013.01)

(58) Field of Classification Search
CPC . A61B 5/6843; A61B 5/14546; A61B 5/1455; A61B 5/6826
See application file for complete search history.

(56) References Cited

U.S. PATENT DOCUMENTS 5,792,052 A * 8/1998 Isaacson ............ A61B 5/02427
600/323
8,437,825 B2 * 5/2013 Dalvi ................. A61B 5/14532
600/310
(Continued)

FOREIGN PATENT DOCUMENTS

JP   2004-267613 A   9/2004
JP   2007-510159 A   4/2007
(Continued)

OTHER PUBLICATIONS

Official Communication issued in International Patent Application No. PCT/JP2014/083758, dated Mar. 31, 2015.

*Primary Examiner* — Lindsey G Wehrheim
(74) *Attorney, Agent, or Firm* — ScienBiziP, P.C.

(57) ABSTRACT

A measuring device that can obtain a stable measurement result is realized. The measuring device includes a measuring portion (14) that is arranged in one of a placing portion (12) where a fingertip portion (A) is placed, and an interposing portion (11) facing the placing portion (12), and interposing, together with the placing portion, the fingertip portion (A), emits excitation light and receives fluorescence, and a fixing force supply portion (13) that supplies, to the fingertip portion (A) through the interposing portion (11), force which is capable of fixing a relative positional relationship between the fingertip portion (A) and the measuring portion (14).

9 Claims, 13 Drawing Sheets

(51) Int. Cl.
    *A61B 5/1455*    (2006.01)
    *A61B 5/145*    (2006.01)

(56) References Cited

U.S. PATENT DOCUMENTS

| | | | |
|---|---|---|---|
| 2008/0076995 A1* | 3/2008 | Hoarau | A61B 5/14552 600/344 |
| 2010/0252721 A1 | 10/2010 | Xu | |
| 2013/0030306 A1 | 1/2013 | Yamanaka et al. | |
| 2013/0197372 A1 | 8/2013 | Hijikuro et al. | |
| 2014/0058227 A1 | 2/2014 | Yamanaka et al. | |
| 2015/0223696 A1 | 8/2015 | Yamanaka | |

FOREIGN PATENT DOCUMENTS

| | | |
|---|---|---|
| JP | 2007-135718 A | 6/2007 |
| JP | 2007-167184 A | 7/2007 |
| JP | 2009-066042 A | 4/2009 |
| JP | 2011-078819 A | 4/2011 |
| JP | 2012-083191 A | 4/2012 |
| JP | 2012-522579 A | 9/2012 |
| JP | 2012-247269 A | 12/2012 |
| JP | 2013-132543 A | 7/2013 |
| JP | 2013-134148 A | 7/2013 |
| JP | 2013-248359 A | 12/2013 |
| WO | 2005/045393 A2 | 5/2005 |
| WO | 2014/045833 A1 | 3/2014 |

\* cited by examiner

RELATIONSHIP BETWEEN WAVELENGTH OF EXCITATION LIGHT AND
WAVELENGTH OF FLUORESCENCE OF AGEs

|  | EXCITATION LIGHT (EXCITATION)(nm) | FLUORESCENCE (EMISSION)(nm) |
|---|---|---|
| CLF COLLAGEN-LINKED FLUORESCENCE | 370 | 440 |
| PENTOSIDINE | 328 (AFTER ACID HYDROLYSIS: 335) | 378 (AFTER ACID HYDROLYSIS: 385) |
| VESPERLYSINES | 370 | 440 |

MEASURING DEVICE

TECHNICAL FIELD

The present invention relates to a measuring device that measures the amount of a fluorescent material based on an intensity of fluorescence which is generated from the fluorescent material within a living body.

BACKGROUND ART

In recent years, the number of lifestyle-related disease patients has increased in accordance with the westernization of a dietary life, and medical and social problems become serious. Currently, it is said that the number of diabetic patients is 8 million in Japan, and the number thereof reaches 20 million if a potential group thereof is included. Three major complications of diabetes are "retinopathy, nephropathy, and neuropathy", and further diabetes becomes a main cause of arteriosclerosis, and even heart disease and brain disease are concerned.

Diabetes occurs from deficiency of insulin which controls a blood glucose level or insulin malfunction, resulting from pancreas malfunction caused by an eating habit disorder, a lifestyle habit disorder, an influence of a secretion from fat cells due to obesity or oxidative stress. If diabetes occurs, the number of times or an amount of urination is increased, and a symptom such as thirst appears, but there is no subjective symptom of the disease in a case of only the symptom, and the disease is mostly discovered by a test in a hospital or the like. This is the reason why there are many "silent" diabetic patients.

There are many cases where the symptoms have already progressed after the abnormal symptoms due to the complications that appear in the hospital or the like, and it is difficult to completely cure the symptoms. In particular, the complication is unlikely to be cured, and prevention is regarded as important in the same manner as other lifestyle-related diseases. Early detection, and curative effect judgment are indispensable in order to perform prevention, and a large number of diabetes tests aiming for that are present.

If oxidative stress is added under an environment where an abnormal amount of carbohydrates or lipids are present in the blood, a reaction of proteins with carbohydrates or lipids occurs, and AGEs (advanced glycation end products) are generated. The AGEs are final products that are formed by a non-enzymatic glycosylation reaction (Maillard reaction) of proteins, and are materials exhibiting yellowish brown color, and emitting fluorescence, and have properties of forming a crosslink by combining with proteins which are present in the vicinity thereof.

The AGES are said to develop arteriosclerosis, by depositing or infiltrating into a wall of a blood vessel, or by acting on macrophage which is in charge of a portion of the immune system and releasing cytokine being one type of protein thereby causing inflammation.

Since the AGEs are also increased in accordance with the increase of blood glucose in the case of diabetes, it is possible to realize early detection of diabetes or grasp the progress state of diabetes, by monitoring the AGEs. In this manner, as a method of screening for diabetes mellitus by monitoring the AGEs, for example, a method disclosed in PTL 1 is reported.

In this method, the AGEs are monitored by irradiating the skin of a forearm with excitation light, and measuring a fluorescence spectrum from the AGEs which are combined with skin collagen, and comparing the measured fluorescence spectrum with a predetermined model. Hereby, data of the AGEs is obtained without invasiveness.

In PTL 2, a detecting device that specifies an optimum position of a relative position between a subject and a light-receiving portion receiving the fluorescence which is emitted by the subject, based on an intensity of the received light which is received by the light-receiving portion, is disclosed.

In PTL 3, a device that monitors the AGEs by being put on an earlobe is disclosed. It is possible to miniaturize the device, by making a relatively small region such as the earlobe in the human body as a measurement target region.

Moreover, technologies disclosed in PTL 4 to PTL 6 are used as examples of measuring devices which make the relatively small region in the human body as a measurement target region although not being monitoring devices for the AGEs. These devices are devices that make a fingertip as a measurement target region, and measure oxygen saturation in blood or a pulse wave.

CITATION LIST

Patent Literature

PTL 1: Japanese Unexamined Patent Application Publication (Translation of PCT Application) No. 2007-510159 (published on Apr. 19, 2007)
PTL 2: Japanese Unexamined Patent Application Publication No. 2012-83191 (published on Apr. 26, 2012)
PTL 3: Japanese Unexamined Patent Application Publication No. 2012-247269 (published on Dec. 13, 2012)
PTL 4: Japanese Unexamined Patent Application Publication No. 2007-135718 (published on Jun. 7, 2007)
PTL 5: Japanese Unexamined Patent Application Publication No. 2007-167184 (published on Jul. 5, 2007)
PTL 6: Japanese Unexamined Patent Application Publication No. 2009-66042 (published on Apr. 2, 2009)

SUMMARY OF INVENTION

Technical Problem

In the configuration described in PTL 1, the AGEs are monitored by placing the forearm being the measurement target region on a placement stand. However, if the fluorescence spectrum is measured by placing the measurement target region on the placement stand as described in PTL 1, since the forearm is not fixed, there is a problem that the intensity (fluorescence intensity) of the measured fluorescence spectrum is not stable. In contrast, in the configurations described in PTL 2 to PTL 6, the measurement target region such as the subject, the earlobe or a finger is fixed to some degree. However, the fixing is not sufficient for fixing the measurement target region, and the problem that a measurement result such as the fluorescence intensity is not stable still remains.

The present invention is made in view of the above problems, and an object of the present invention is to realize a measuring device that can obtain a stable measurement result.

Solution to Problem

In order to solve the above problems, a measuring device according to one aspect of the present invention is a measuring device measuring an amount of a fluorescent material, based on an intensity of fluorescence that is generated from the fluorescent material within a living body excited by excitation light with which a measurement target region of the living body is irradiated, the device includes a placing portion where the measurement target region is placed, an interposing portion that faces the placing portion, and interposes, with the placing portion, the measurement target region, an emitting portion that is arranged in one of the placing portion and the interposing portion, and emits the excitation light, a light-receiving portion that is arranged in one of the placing portion and the interposing portion, and receives the fluorescence, and a fixing force supply portion that supplies, to the measurement target region through the interposing portion, force which is capable of fixing a relative positional relationship between the measurement target region and the light-receiving portion.

The intensity of the fluorescence which is generated from the measurement target region, depends on a distance between a blood vessel position of the measurement target region where the fluorescent material is present and the light-receiving portion. Hence, if the measurement target region is not sufficiently fixed, the distance between the blood vessel position and the light-receiving portion is changed by elasticity of the measurement target region or the like, and the intensity of the fluorescence is not stable. Here, according to the configuration described above, the force which is capable of fixing the relative positional relationship between the measurement target region and the light-receiving portion is supplied to the measurement target region through the interposing portion. That is, the force which is generated by the fixing force supply portion is transmitted to the interposing portion, and the force which is transmitted to the interposing portion is supplied to the measurement target region. Hereby, the distance between the blood vessel position of the measurement target region and the light-receiving portion is fixed, and since it is possible to suppress that the distance is changed along with the elapse of time, it is possible to stabilize the intensity of the measured fluorescence. Namely, it is possible to obtain a stable measurement result.

In the measuring device according to one aspect of the present invention, the placing portion and the interposing portion may have facing faces which face each other in a state of interposing the measurement target region therebetween, and the light-receiving portion may protrude from the facing face of the placing portion or the interposing portion.

According to the configuration described above, since the light-receiving portion protrudes from the facing face, it is possible to strongly press a tip of the light-receiving portion against the measurement target region. That is, the measurement target region is pressed against the tip of the light-receiving portion of which an area is smaller than that of the facing face. Hereby, when the force which is supplied from the fixing force supply portion is uniform, the force (pressure) per unit area which is supplied to the measurement target region becomes large. In other words, in order to obtain the force that is capable of fixing the relative positional relationship between the measurement target region and the light-receiving portion, it is possible to make the force which is supplied from the fixing force supply portion be small in comparison with a configuration in which the light-receiving portion does not protrude. Accordingly, even if the force which is supplied by the fixing force supply portion is made to be smaller, it is possible to stabilize the intensity of the measured fluorescence.

Moreover, the measuring device according to one aspect of the present invention may further include an outer edge portion that is formed on a periphery of the light-receiving portion, and the outer edge portion may have an outer edge contact face which contacts with the measurement target region.

According to the configuration described above, the outer edge portion is formed on the periphery of the light-receiving portion. Hereby, in the configuration in which the light-receiving portion protrudes from the facing face, the area which is in contact with the measurement target region becomes wide, in comparison with a configuration in which the outer edge portion is not included. Accordingly, it is possible to relieve pain which may be generated in the measurement target region, in comparison with the configuration in which the outer edge portion is not included.

Moreover, the measurement target region is pressed against the outer edge contact face of which the area is smaller than that of the facing face. Hereby, when the force which is supplied from the fixing force supply portion is uniform, the pressure which is supplied to the measurement target region becomes large, in comparison with a configuration in which the outer edge portion is not included, and the light-receiving portion does not protrude. In other words, in order to obtain the force that is capable of fixing the relative positional relationship between the measurement target region and the light-receiving portion, it is possible to make the force which is supplied from the fixing force supply portion be small in comparison with the configuration in which the outer edge portion is not included, and the light-receiving portion does not protrude. Accordingly, even if the force which is supplied by the fixing force supply portion is made to be smaller, it is possible to stabilize the intensity of the measured fluorescence.

In the measuring device according to one aspect of the present invention, the light-receiving portion may have a light-receiving face which receives the fluorescence, and a concave portion may be formed by positioning the light-receiving face at a position which is deeper than the outer edge contact face.

According to the configuration as described above, the light-receiving face of the light-receiving portion is positioned at the position which is deeper than the outer edge contact face. Hereby, since the measurement target region does not contact with the light-receiving face at the time of the measurement, it is possible to maintain the light-receiving face which receives the fluorescence in a clean state.

In the measuring device according to one aspect of the present invention, a detachable light-transmitting member may be arranged on the outer edge contact face.

According to the configuration described above, since the measurement target region contacts with the light-transmitting member at the time of the measurement, the measurement target region does not contact with the light-receiving face of the light-receiving portion. Accordingly, it is possible to maintain the light-receiving face in the clean state.

Since the light-transmitting member is detachable, it is possible to change the light-transmitting member whenever a user using the measuring device is changed. Accordingly, it is possible to achieve an improvement of the sanitation.

Moreover, the measuring device according to one aspect of the present invention may further include a mirror face portion that reflects the fluorescence which is incident and that is provided on a side face within the concave portion.

According to the configuration described above, the measurement target region and the light-receiving face which receives the fluorescence are separated by the concave portion. Therefore, there is concern that the intensity of the fluorescence reaching the light-receiving face is weakened, by that the fluorescence which is emitted from the measurement target region is absorbed into the side face within the concave portion.

Here, according to the configuration described above, since the mirror face portion is provided on the side face within the concave portion, the fluorescence is reflected by the mirror face portion. Accordingly, since the fluorescence may be incident to the light-receiving face, in a state of suppressing that the intensity of the fluorescence which is emitted from the measurement target region is weakened, it is possible to efficiently concentrate the fluorescence.

The measuring device according to one aspect of the present invention may further include a fixing force sensor that measures a value of force which is applied by the fixing force supply portion, and a fixing force control portion that controls the fixing force supply portion such that the force which is applied by the fixing force supply portion is a predetermined value or more, depending on a measurement result by the fixing force sensor.

According to the configuration described above, the fixing force supply portion controls the force which is applied to the measurement target region to be the predetermined value or more, depending on the measurement result by the fixing force sensor. That is, only by making the predetermined value as a value such that a time-dependent change in the intensity of the fluorescence does not occur, it is possible to stabilize the intensity of the fluorescence.

In the measuring device according to one aspect of the present invention, the measurement target region may be a fingertip.

According to the configuration described above, the measurement target region is the fingertip. Since melanin is not mostly present in the palm including the fingertip, special consideration is not necessary for the absorption of the excitation light by melanin. That is, it is possible to perform the measurement by excluding an influence of sunburn or an influence due to a difference between the races (whether being the non-white race or the white race). Moreover, when the fluorescent materials within the living body are the advanced glycation endproducts (AGEs), since the finger being a peripheral organ is a spot where the AGEs are likely to be collected, it is possible to improve accuracy of the measurement by making the fingertip as a measurement target region.

Advantageous Effects of Invention

According to one aspect of the present invention, an effect of realizing a measuring device which can obtain a stable measurement result is achieved.

BRIEF DESCRIPTION OF DRAWINGS

FIG. 7(a) is a sectional view illustrating a portion of a measuring device for the comparison, and FIG. 7(b) is a graph illustrating the time-dependent change of the intensity of the fluorescence which is measured by the measuring device illustrated in FIG. 7(a).

DESCRIPTION OF EMBODIMENTS

Embodiment 1

Figure 1:
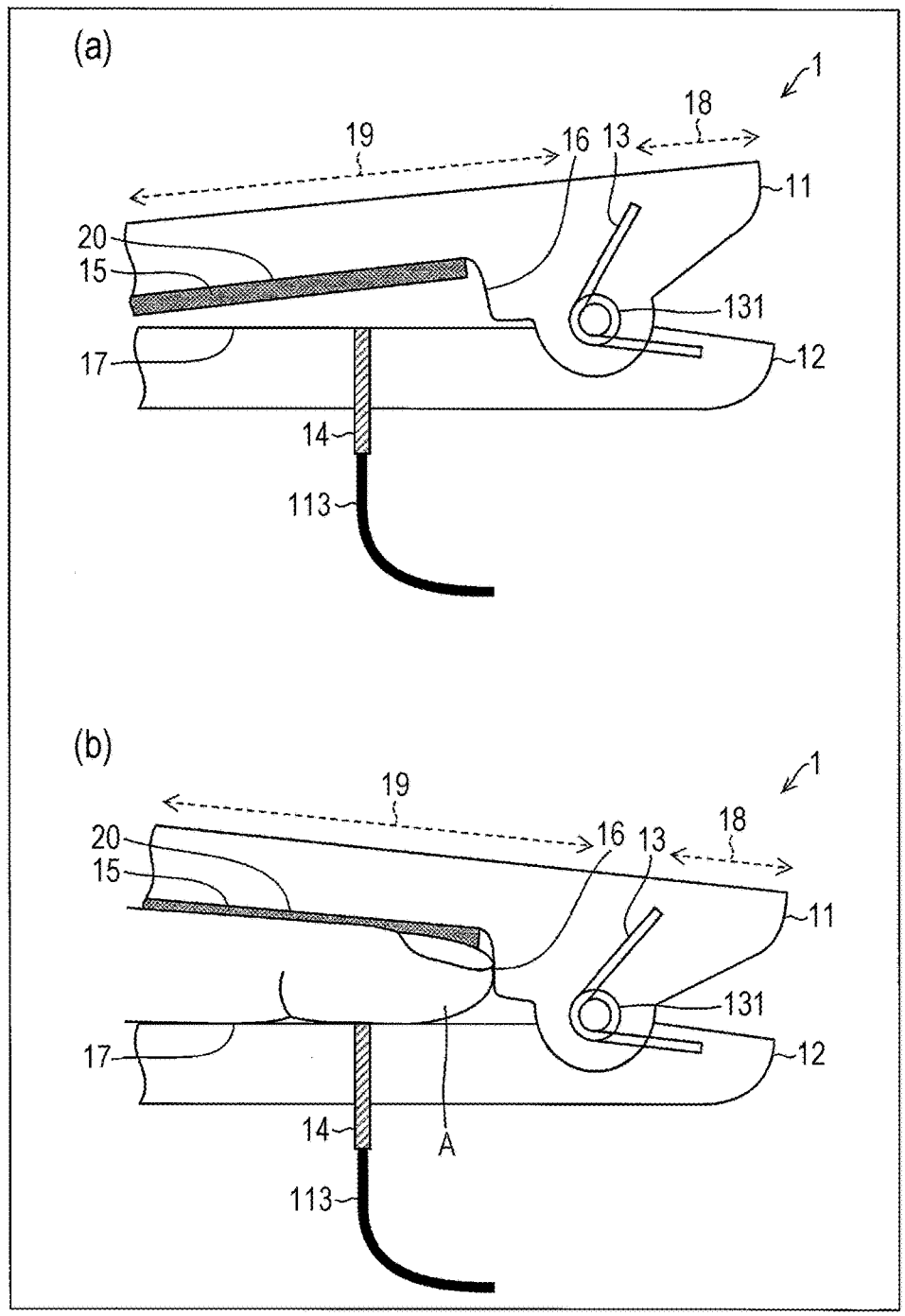
FIG. 1 illustrates sectional views of a fingertip measuring unit according to Embodiment 1.

Hereinafter, embodiments of the present invention will be described in detail. In the embodiments described hereinafter, an example in which the present invention is applied to a measuring device that measures the amount of advanced glycation endproducts (AGEs) as a fluorescent material which emits fluorescence by being excited with light (excitation light) having a specific wavelength, will be described. Moreover, in the embodiments described hereinafter, an example in which the present invention is applied to a fingertip measuring device that measures the amount of the fluorescent material, based on an intensity of the fluorescence that is generated from the fluorescent material which is present in the fingertip portion by irradiating a fingertip (referred to as fingertip portion, hereinafter) with the excitation light, will be described. Furthermore, an application example is not limited to the fingertip measuring device, and if being the measuring device that measures the amount of the fluorescent material, based on the intensity of the fluorescence that is generated from the fluorescent material within a living body excited by the excitation light with which a measurement target region is irradiated within the living body, it is possible to apply the present invention thereto. In this case, an arm, a wrist, a palm of a hand, an earlobe or the like is exemplified as the measurement target region described above.

However, by making the fingertip portion as a measurement target region, there is a merit as illustrated hereinafter. First, since the fingertip portion is a region where the AGEs is likely to be accumulated, and determination of a measurement position or a fixing thereof becomes easy, it is possible to improve accuracy of the measurement, by making the fingertip portion as a measurement target region. Moreover, since melanin is not mostly present in the fingertip portion, special consideration is not necessary for the absorption of the excitation light by melanin at the time of measuring the fluorescence. That is, it is possible to perform the measurement by excluding an influence of sunburn or an influence due to a difference between the races. Furthermore, it is possible to miniaturize the measuring device (particularly, a measuring unit for placing the measurement target region), in comparison with a case of making the arm or the wrist as a measurement target region.

For convenience of the description, the same sign is attached to a member having the same function as a member illustrated in each embodiment, and the description thereof will be appropriately omitted. Furthermore, dimensions such as a shape, a length, a size and a width of a configuration which is described in each drawing, do not reflect the actual shape and dimensions, and are appropriately changed for clarification and simplification of the drawings.

Embodiment 1

If being described based on FIG. 1 to FIG. 6, one embodiment of the present invention is described as follows.
(Configuration of Fingertip Measuring Device 100)

Figure 2:
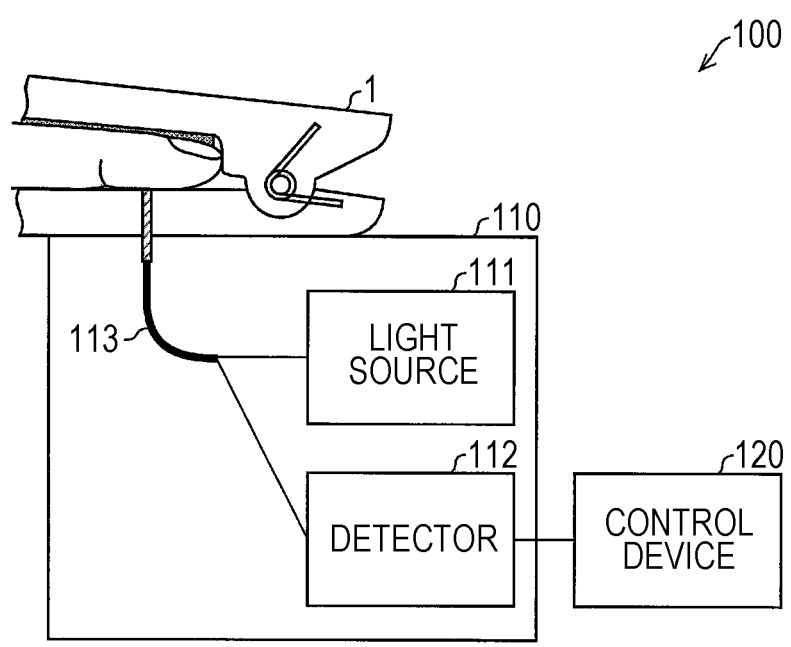
FIG. 2 is a diagram illustrating an example of a configuration of a fingertip measuring device.
Figure 3:
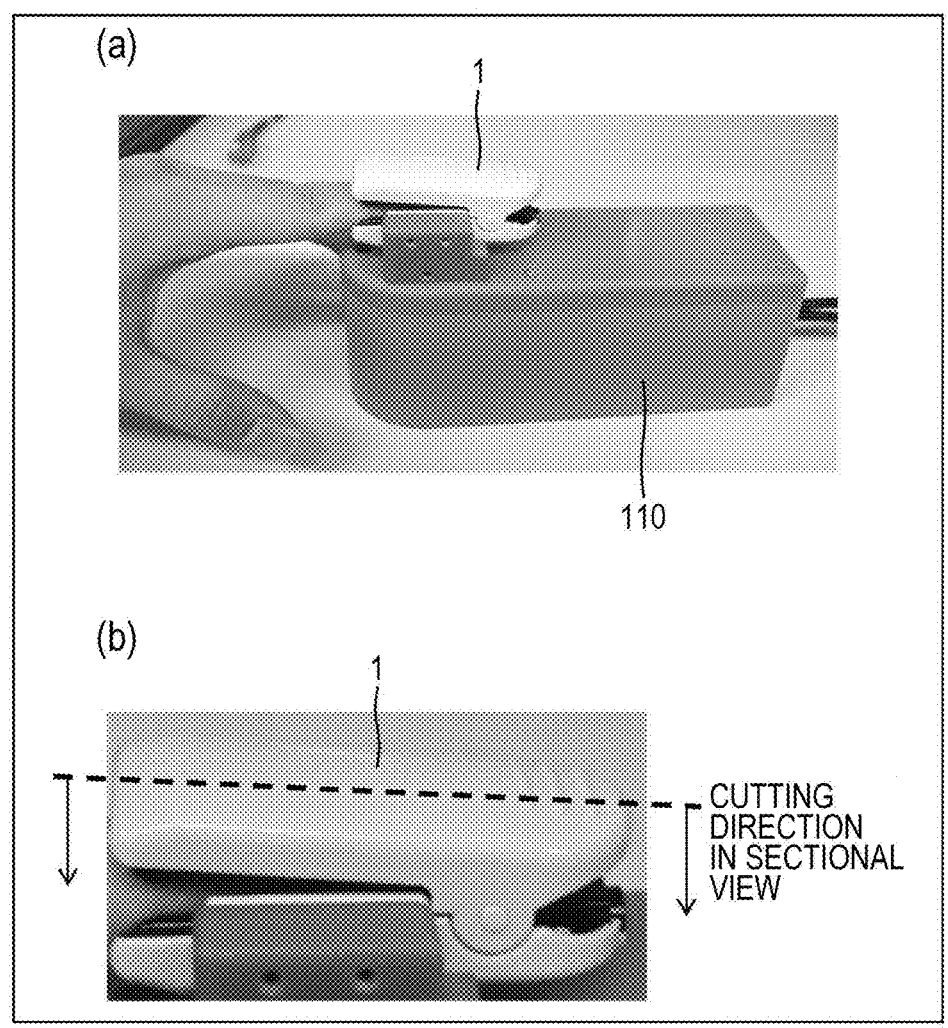
FIG. 3(a) and FIG. 3(b) are diagrams illustrating a fingertip measuring unit and a measuring member arrangement portion which are included in the fingertip measuring device of FIG. 2.
Figures 4, 5:
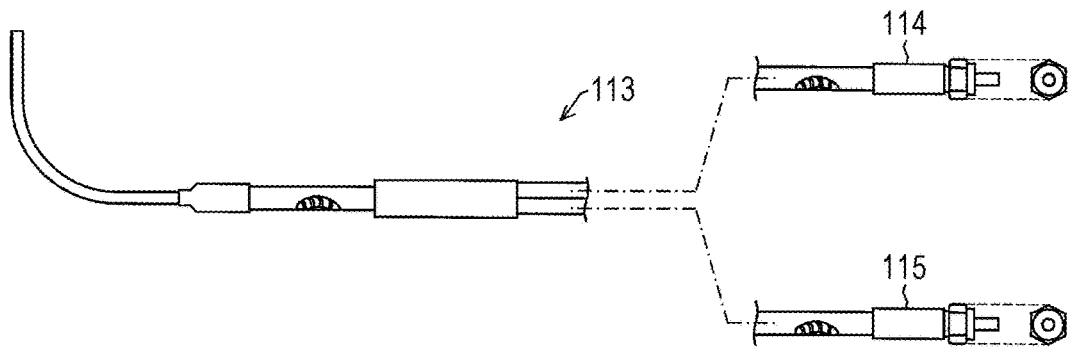
FIG. 4 is a view illustrating a measuring probe which is included in the fingertip measuring device of FIG. 2.
FIG. 5 is a table expressing a relationship between a wavelength of excitation light and a wavelength of fluorescence in AGEs.

First, a configuration of a fingertip measuring device 100 according to the present invention will be described with reference to FIG. 1 to FIG. 5. FIG. 1 is a sectional view illustrating a fingertip measuring unit 1 according to Embodiment 1. Moreover, FIG. 2 is a diagram illustrating an example of a configuration of a fingertip measuring device 100. FIG. 3 is a diagram illustrating the fingertip measuring unit 1 and a measuring member arrangement portion 110 which are included in the fingertip measuring device 100 of FIG. 2. Still more, FIG. 4 is a view illustrating a measuring probe 113 which is included in the fingertip measuring device 100 of FIG. 2. FIG. 5 is a table expressing a relationship between a wavelength of the excitation light and a wavelength of the fluorescence in the AGEs.

As illustrated in FIG. 2, the fingertip measuring device 100 (measuring device) according to Embodiment 1 is configured to include the fingertip measuring unit 1, the measuring member arrangement portion 110, and a control device 120.

As illustrated in FIG. 1(b), the fingertip measuring unit 1 is a unit into which a user (subject) inserts a finger (fingertip portion A) of the user in order to measure the AGEs. As illustrated in FIG. 3(a), the fingertip measuring unit 1 is arranged on the measuring member arrangement portion 110. As illustrated in FIG. 3(a), the user may measure the AGEs which are present within a blood vessel in the fingertip portion A of the user, by inserting an index finger into the fingertip measuring unit 1. Moreover, the fingertip measuring unit 1 fixes the inserted finger of the user. Furthermore, details of the fingertip measuring unit 1 will be described later. In Embodiment 1, the index finger is exemplified as a finger which is inserted into the fingertip measuring unit 1, but the finger which is inserted into the fingertip measuring unit 1 is not particularly limited, and for example, a middle finger may be used. Furthermore, the sectional view of the fingertip measuring unit which is described in FIG. 1 and other embodiments is a sectional view in a case of cutting the fingertip measuring unit by a dotted line illustrated in FIG. 3(b).
(Measuring Member Arrangement Portion 110)

The measuring member arrangement portion 110 is a portion where the members for measuring the fluorescence which is derived from the AGEs are arranged. The measuring member arrangement portion 110 is configured to include a light source 111, a detector 112, and a measuring probe 113.
(Light Source 111)

The light source 111 is a light source that generates the excitation light with which the fingertip portion A is irradiated. The excitation light is the light for detecting the fluorescence which is derived from the AGEs, and has a wavelength range which is suitable to detect the AGEs. As a type of the light source which is used as a light source 111, a tubular bulb type such as a halogen or xenon light source, an LED (manufactured by Nichia Corporation or DOWA Electronics Materials Co., Ltd.), an LD or the like may be used.

Subsequently, the wavelength range of the excitation light which is generated by the light source 111 will be described in detail. In the AGEs, there are types of approximately 20 even if being merely currently known, and there are many types of emitting the fluorescence if being irradiated with the light therein. Examples thereof are illustrated in FIG. 5.

In a table of FIG. 5, CLF (collagen-linked fluorescence) is the fluorescence from the AGEs which is linked to collagen, and is used as a general measure of gross production of the AGEs and a collagen crosslink which is associated therewith.

Pentosidine, and Vesperlysine are typical examples of the AGEs. Pentosidine has a structure in which pentose, equimolar lysine, and arginine are cross-linked, and becomes a suitable fluorescent material after acid hydrolysis. The pentosidine is reported to be particularly increased in the occurrence of diabetes or nephropathy of an end stage. Vesperlysine has a structure in which bovine serum albumin (BSA) with the AGEs is isolated as a main fluorescent material after acid hydrolysis, and lysine of two molecules are cross-inked. For example, glucosepane or the like is used as an example of the AGEs which are not illustrated in FIG. 5.

As understood from the table of FIG. 5, the wavelength of 365 nm, or the wavelength in the vicinity thereof is most suitable as a wavelength of the excitation light which is emitted by the light source 111. However, since there is the width in the excitation light depending on the types of the AGEs, the light of 400 nm to 600 nm being a field of visible light from 315 nm to 400 nm being a field of UVA, may be used as a wavelength of the excitation light which is emitted by the light source 111.
(Detector 112)

The detector 112 receives the fluorescence which is generated by that the fingertip portion A is irradiated with the excitation light, and measures the wavelength of the fluorescence, and the intensity of the fluorescence per wavelength. That is, the detector 112 measures whether the fluorescence having a certain wavelength is detected by strength of the certain degree. As a detector 112, a CCD detector (ILX511B; manufactured by SONY Corporation), a photodetector (SiPIN photodiode; manufactured by Hamamatsu Photonics K.K.), a semiconductor detector such as a CMOS image sensor, a photomultiplier tube (PMT), a channeltron detector or the like may be used.

Since the wavelength of the fluorescence is longer than that of the excitation light, it is favorable as a detector 112 if being capable of detecting the light in the range of 350 nm to 500 nm. However, as understood from the table of FIG. 5, since there is the width of the wavelength which is detected depending on the types of the AGEs in the fluorescence, it may be used as a detector 112 if being capable of detecting the light in the range of 320 nm to 900 nm. Furthermore, the detector 112 may include a spectroscope.

By detecting the fluorescence in this manner, the fingertip measuring device 100 can noninvasively measure the amount of the AGEs which are present in the blood vessel.

(Measuring Probe 113)

The measurement probe 113 functions as an excitation light irradiation portion that irradiates a specific position in a skin surface of the fingertip portion A with the excitation light, and a fluorescence-receiving portion that receives the fluorescence which is generated by that the specified position is irradiated with the excitation light. That is, the measuring probe 113 is a combination of the excitation light irradiation portion and the fluorescence-receiving portion.

As illustrated in FIG. 4, the measuring probe 113 is an incidence-emission coaxial system optical fiber, and includes a fiber for incidence 114 that guides the excitation light from the light source 111 to the specific position, and a fiber for emission 115 that guides the fluorescence which is generated in the specific position to the detector 112. In the measuring probe 113, an end portion of a side where the fiber for incidence 114 and the fiber for emission 115 are integrated, is connected to the fingertip measuring unit 1. Moreover, the other end portion is separated into the fiber for incidence 114 and the fiber for emission 115, and the fiber for incidence 114 is connected to the light source 111, and the fiber for emission 115 is connected to the detector 112. Hereby, it is possible to irradiate the specific position of the fingertip portion A with the excitation light, and it is possible to guide the fluorescence which is emitted from the fingertip portion A to the detector 112. Still more, the fiber for incidence 114, and the fiber for emission 115 may be arranged as individual fibers which are not coaxial fibers.

(Control Device 120)

The control device 120 is favorable if being a device that is capable of adjusting luminance of the light source 111, controlling a switching of irradiation or non-irradiation, storing data, displaying data, analyzing data and the like, and for example, is a personal computer. Moreover, the control device 120 displays a fluorescence spectrum on a monitor which is not illustrated, based on a detection result (intensity of the fluorescence per wavelength) which is input from the detector 112. Furthermore, the control device 120 may calculate an accumulation amount (fluorescent material amount) of the fluorescent materials such as the AGEs that are accumulated in a blood vessel wall of the fingertip portion A, from the detection result which is input from the detector 112. The control device 120 may convert the calculated fluorescent material amount into an index (for example, health state levels of five steps) of understanding a health state of the user, and may provide the information that is easily understandable for the user, by displaying the conversion on the monitor which is not illustrated.

(Details of Fingertip Measuring Unit 1)

Figure 6:
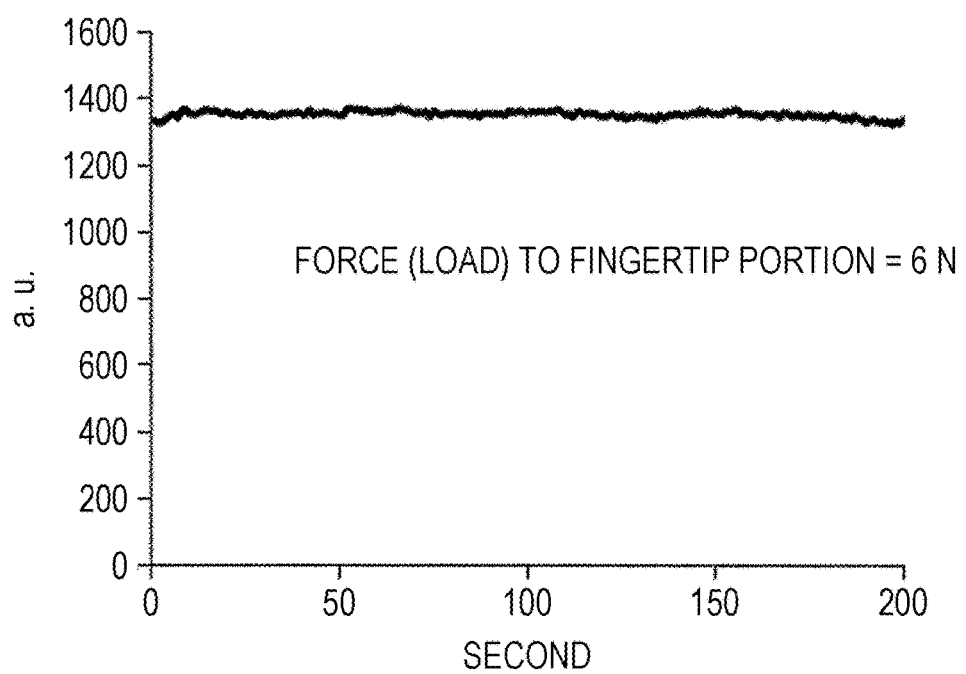
FIG. 6 is a graph illustrating a time-dependent change of an intensity of the fluorescence which is measured by the fingertip measuring device of FIG. 2.
Figure 7:
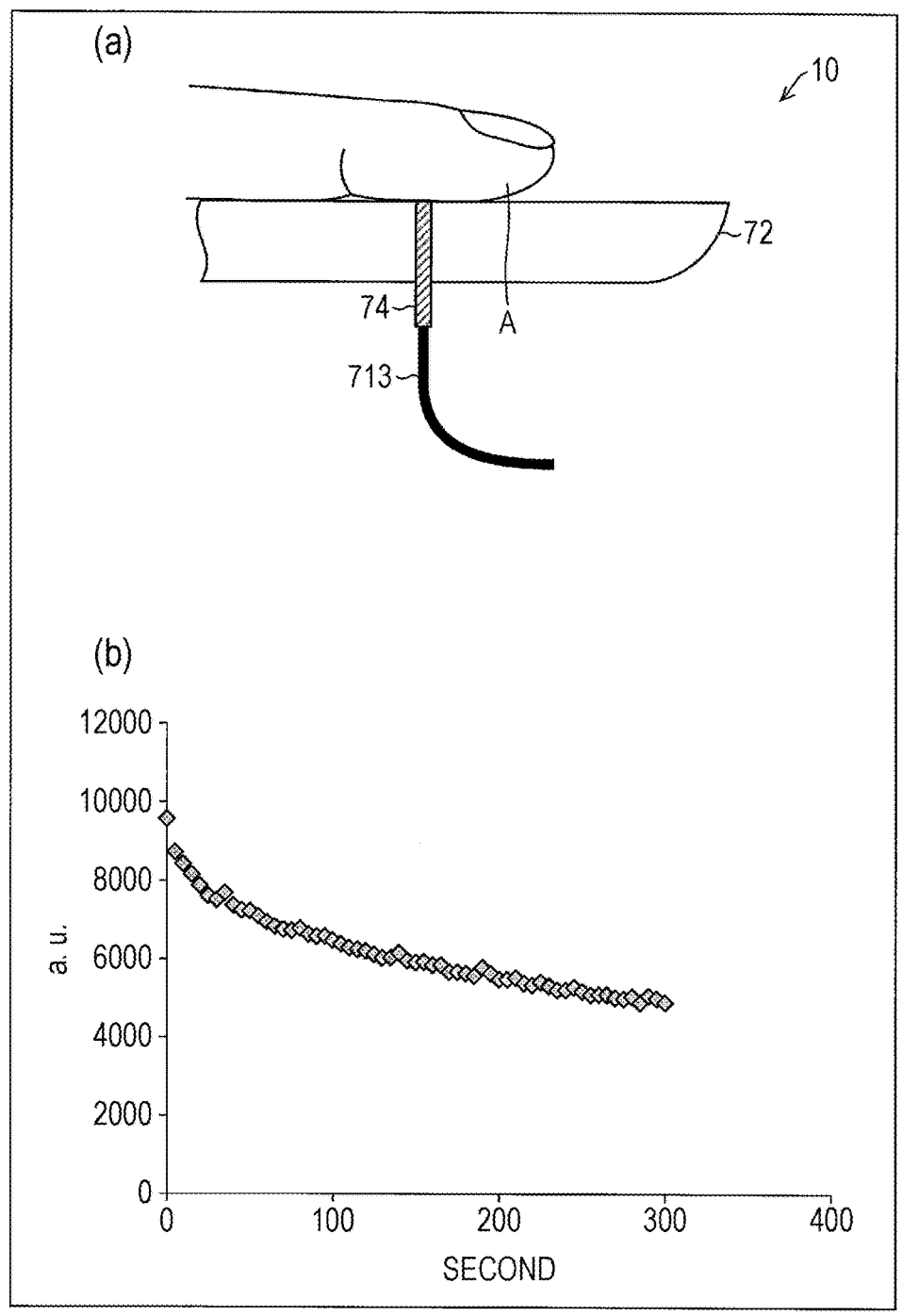
FIG. 7(a) and FIG. 7(b) are diagrams for comparing with the fingertip measuring unit of FIG. 1.

Next, the details of the fingertip measuring unit 1 according to Embodiment 1, will be described with reference to FIG. 1, FIG. 6 and FIG. 7. FIG. 6 is a graph illustrating a time-dependent change of the intensity of the fluorescence which is measured by the fingertip measuring device 100 of FIG. 2. Moreover, FIG. 7 is a diagram for comparing with the fingertip measuring unit 1 of FIG. 1, and FIG. 7(a) is a sectional view illustrating a portion of a measuring device 10 for the comparison, and FIG. 7(b) is a graph illustrating the time-dependent change of the intensity of the fluorescence which is measured by the measuring device 10 illustrated in FIG. 7(a). As illustrated in FIG. 1, the fingertip measuring unit 1 according to Embodiment 1, is configured to include an interposing portion 11, a placing portion 12, a fixing force supply portion 13, and a measuring portion 14 (emitting portion, light-receiving portion).

(Placing Portion 12)

The placing portion 12 is a member (stand portion) that is capable of placing the measurement target region so as to be in contact with a placing face 17 (facing face). As illustrated in FIG. 1(b), in Embodiment 1, the finger which includes the fingertip portion A being the measurement target region is placed on the placing face 17 of the placing portion 12. Moreover, the placing portion 12 is connected to a measuring portion 14 described later, and a measuring face (measuring face 143 illustrated in FIG. 9(b)) is formed in the end portion of the measuring portion 14. The measuring face is an emitting face that emits the excitation light, and a light-receiving face that receives the fluorescence which is emitted from the fingertip portion A. Still more, the measuring face is exposed by the same height as the placing face 17. Hereby, as illustrated in FIG. 1(b), if the fingertip portion A is placed in the placing portion 12, the measuring face 143 of the measuring portion 14 is in contact with the fingertip portion A.

(Interposing Portion 11)

The interposing portion 11 is a member (pressing plate) that faces the placing portion 12, and interposes, with the placing portion 12, the measurement target region. Specifically, the user may insert the fingertip portion A between the placing portion 12 and a pinch portion 19 of the interposing portion 11, by pressing a knob portion 18. If the pressing of the knob portion 18 is stopped after the user inserts the fingertip portion A, the fingertip portion A is interposed by the placing portion 12 and the pinch portion 19. That is, in a state where the finger is not inserted, the interposing portion 11 faces the placing portion 12, so that a tip portion of the interposing portion 11, and a tip portion of the placing portion 12 are in contact with each other or are close to each other. The tip portions are tip portions of opposite sides to a position which is connected to the fixing force supply portion 13, and are tip portions into which the finger is inserted.

The interposing portion 11 may include a buffering portion 15, and a positioning portion 16. The buffering portion 15 is included on a face (facing face 20) which faces the placing face 17 of the placing portion 12. The facing face 20 is in contact with the inserted finger of the user in the pinch portion 19. Moreover, the facing face 20 is a face that transmits the force (for example, restoring force) which is generated by the fixing force supply portion 13 described later as the force (load) which is applied to the measurement target region, to the finger. When the buffering portion 15 is not included, since the finger of the user is in contact directly with the pinch portion 19, there is concern that the user feels the pain. Therefore, by including the buffering portion 15 on the facing face 20 which is in contact with the finger of the user in the pinch portion 19, the load which is applied to the fingertip portion A is equalized throughout the finger, and it is possible to reduce the pain which the user feels by the local pressing. As a material for the buffering portion 15, a rubber sponge, a biocompatible elastomer or the like exemplified.

Moreover, the positioning portion 16 is a member that performs a positioning of the fingertip portion A being the measurement target region in the placing face 17, by defining the position of the tip of the inserted finger (fingertip portion A) of the user. Specifically, the positioning portion 16 is a portion of a surface of the pinch portion 19 which the tip of the inserted finger of the user touches, and is a face that forms a substantially right angle with the face (facing face 20) where the buffering portion 15 is included in the pinch portion 19, in FIG. 1(b). The user may make a position which is in contact with the measuring face 143 of the measuring portion 14 in the fingertip portion A into almost the same position at all times, by placing the finger in the placing portion 12 so that the positioning portion 16 is in contact with the tip of the fingertip portion A. Hereby, since a distance between the measuring face 143 and a blood vessel position of the fingertip portion A is substantially the same, it is possible to suppress the deviation of the measurement by changing the measurement position. The positioning portion 16 of Embodiment 1 is formed in the interposing portion 11, but is not limited thereto. For example, the positioning portion 16 may be formed in the placing portion 12. Moreover, the positioning portion 16 of Embodiment 1 determines the position of only an X axis direction (insertion direction of the finger) when an XY plane is defined with respect to the placing face 17, but is not limited thereto. For example, the position of not only the X axis direction but also a Y axis direction (direction which is substantially perpendicular to the insertion direction of the finger in the placing face 17) may be determined. Specifically, in order to determine the position in the Y axis direction, for example, a convex portion which is extended in the direction of the interposing portion 11, may be formed at a position which is separated from the measuring face 143 (see FIG. 9(b)) by a predetermined distance in the Y axis direction of the placing face 17. For example, the predetermined distance is favorable if being a distance of the degree that the vicinity of a center of the fingertip portion A of the finger of an average adult is placed on the measuring face 143.

(Fixing Force Supply Portion 13)

The fixing force supply portion 13 is a member that supplies the force which is capable of fixing a relative positional relationship between the measurement target region and the measuring portion 14 to the measurement target region through the interposing portion 11. The fixing force supply portion 13 of Embodiment 1 is a spring type hinge. The interposing portion 11 is coupled to the placing portion 12 so as to be rotatable by using a coupling portion 131 which is included in the interposing portion 11 as a rotation axis. The fixing force supply portion 13 is arranged in the vicinity of the coupling portion 131, so that the interposing portion 11 is rotated in a direction of approaching the placing portion 12 by using the coupling portion 131 as a rotation axis. That is, in Embodiment 1, the fingertip measuring unit 1 has a so-called clip structure. In the fingertip measuring unit 1, by that the user presses the knob portion 18 of the interposing portion 11, the restoring force of returning to the state of FIG. 1(a) acts upon the fixing force supply portion 13. Here, if the finger is inserted between the pinch portion 19 of the interposing portion 11 and the placing portion 12 as illustrated in FIG. 1(b), and the pressing of the knob portion 18 is stopped, the restoring force is transmitted to the interposing portion 11. Therefore, the restoring force which is transmitted to the interposing portion 11 is supplied to the fingertip portion A as load. Hereby, the relative positional relationship between the fingertip portion A and the measuring portion 14 is fixed. In other words, the fingertip portion A is fixed in the state of being pressed against the measuring face 143 of the measuring portion 14 and the placing face 17.

Here, if the load which is supplied to the fingertip portion A is small, the relative positional relationship between the blood vessel position of the fingertip portion A and the measuring portion 14 may be changed during the measurement, by elasticity of the fingertip portion A. Hence, the load which is supplied to the fingertip portion A is necessary to be the load of the degree that the relative positional relationship between the fingertip portion A and the measuring portion 14 is fixed. Since the distance between the blood vessel position within the fingertip portion A and the measuring portion 14 (measuring face 143 of the measuring portion 14) is fixed by fixing the relative positional relationship between the fingertip portion A and the measuring portion 14, the detection result (intensity of the detected fluorescence) is stable. The inventors of the present specification found out that the load which was supplied to the fingertip portion was approximately 3N in an existing measuring device (for example, a device that measures oxygen saturation or a pulse wave by interposing the fingertip portion), and the intensity of the fluorescence was not stable in the load of 3N. That is, in the case of the fingertip measuring unit 1, it is preferable that the load which is supplied to the fingertip portion A is larger than 3N. Furthermore, the inventors of the present specification found out that if being the structure of the fingertip measuring unit 1, the intensity of the fluorescence was stable when the load which was supplied to the fingertip portion A was 6N as illustrated in FIG. 6. That is, in the case of the structure of the fingertip measuring unit 1, the load which is transmitted to the fingertip portion A is more preferably 6N or more, and it is preferable that the fixing force supply portion 13 is capable of generating the force (restoring force) so as to supply the load of 6N or more to the fingertip portion A. If the load which is supplied to the fingertip portion A is too large, since the pain may occur in the fingertip portion A, it is preferable that an upper limit of the load is approximately 9N.

On the other hand, as illustrated in FIG. 7(a), in the case of the measuring device 10 that performs the measurement of the intensity of the fluorescence by placing the fingertip portion A in a placing portion 72 without including the fixing force supply portion 13, the intensity of the measured fluorescence is decreased along with the elapse of time, as illustrated in FIG. 7(b). This is because that the distance between a measuring portion 74 and the blood vessel position of the fingertip portion A becomes long, by that the shape of the fingertip portion A is changed due to elasticity of the fingertip portion A, since the load is not supplied to the fingertip portion A from the interposing portion 11 (relative positional relationship is not fixed) by the restoring force from the fixing force supply portion 13. Here, since the placing portion 72, the measuring portion 74, and a measuring probe 713 which are illustrated in FIG. 7(a) are similar to the placing portion 12, the measuring portion 14, and the measuring probe 113 of the fingertip measuring unit 1, the detailed description will be omitted.

(Measuring Portion 14)

The measuring portion 14 is an end portion (measurement attachment) of the side where the fiber for incidence 114 and the fiber for emission 115 of the measuring probe 113 described above are integrated. That is, the measuring portion 14 is a portion where the functions of the emitting portion which emits the excitation light and the light-receiving portion which receives the fluorescence are integrated. As described above, if the measuring face 143 of the measuring portion 14 is exposed (is present within the plane including the placing face 17) by the same height as the placing face 17, and the fingertip portion A is placed in the placing portion 12, the measuring face 143 is in contact with the fingertip portion A. Hereby, the excitation light is emitted from the measuring face 143 of the measuring portion 14 toward the fingertip portion A, and the fluorescence which is emitted from the fingertip portion A by receiving the excitation light, is received by the measuring face 143. Accordingly, the measuring portion 14 may irradiate the contact fingertip portion A with the excitation light, and may receive the fluorescence from the fluorescent materials (AGEs) which are present in the blood vessel within the fingertip portion A.

Effects of Invention According to Embodiment 1

The intensity of the fluorescence from the fluorescent materials (AGEs) which are present in the blood vessel within the fingertip portion A, depends on the distance between the blood vessel position and the measuring portion 14. Hence, if the fingertip portion A is not sufficiently fixed, the distance between the blood vessel position and the measuring portion 14 may be slightly changed by elasticity of the fingertip portion A, and the intensity of the fluorescence is not stable. Here, according to the fingertip measuring unit 1 of Embodiment 1, the load is added to the fingertip portion A through the interposing portion 11 by the restoring force of the fixing force supply portion 13 (spring type hinge). Hereby, since it is possible to suppress that the distance between the blood vessel position of the fingertip portion A and the measuring portion 14 is changed along with the elapse of time, it is possible to stabilize the intensity of the measured fluorescence.

Embodiment 2

Figure 8:
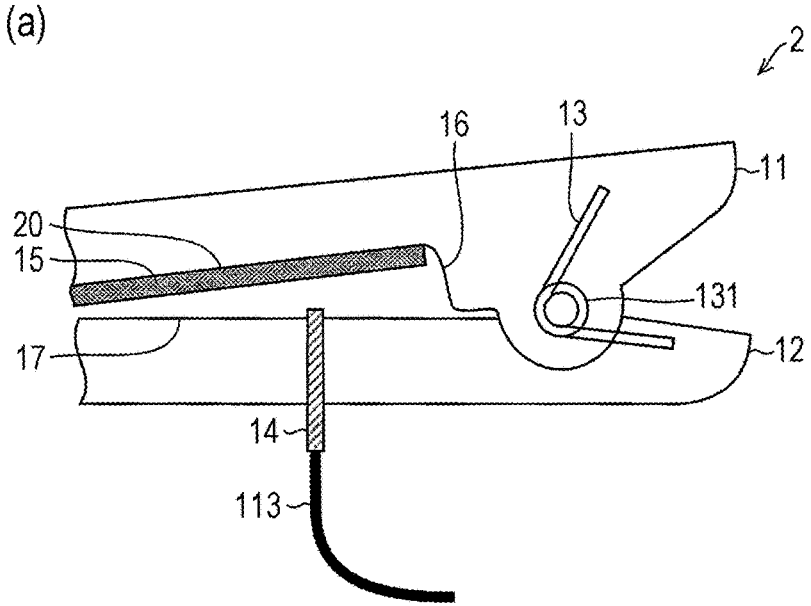
FIG. 8(a) and FIG. 8(b) are sectional views illustrating a fingertip measuring unit according to Embodiment 2.
Figure 8:
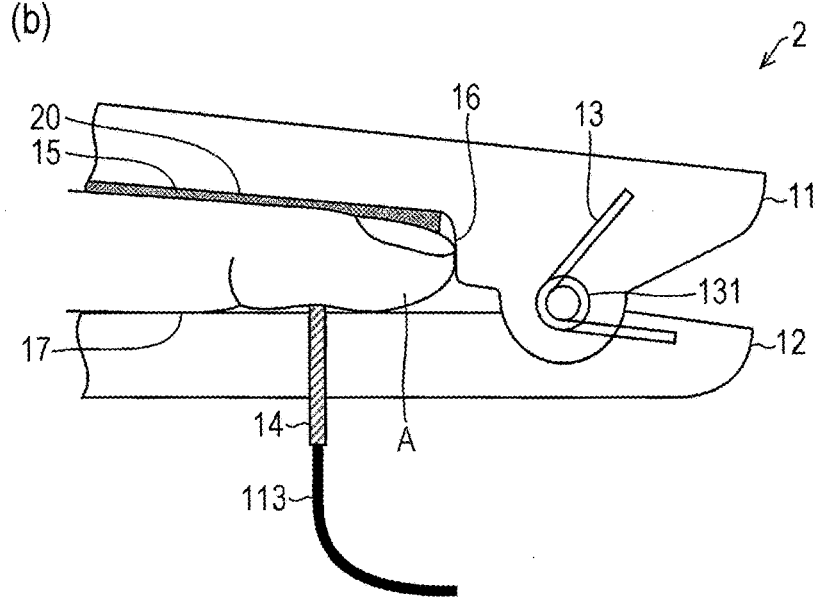

If being described based on FIG. 8, another embodiment of the present invention is described as follows. FIG. 8 is a sectional view illustrating a fingertip measuring unit 2 according to Embodiment 2.

As illustrated in FIG. 8(a), the fingertip measuring unit 2 according to the Embodiment 2 has a configuration in which the measuring portion 14 protrudes from the placing face 17 of the placing portion 12. In other words, the measuring face 143 of the measuring portion 14 is configured to be closer to the placed fingertip portion A than the placing face 17. Hereby, as illustrated in FIG. 8(b), if the fingertip portion A is placed in the placing portion 12, and the load is added to the fingertip portion A through the interposing portion 11 by the restoring force of the fixing force supply portion 13, the fingertip portion A is strongly pressed against the protruding portion (measuring face 143) of the measuring portion 14.

Hereby, since the fingertip portion A is pressed against the measuring face 143 of which an area is smaller than that of the placing face 17, when the load which is supplied to the fingertip portion A is uniform, the load (load pressure) per unit area which is supplied to the fingertip portion A becomes large, in comparison with the fingertip measuring unit 1 according to Embodiment 1. In other words, in order to obtain the load which is capable of fixing the relative positional relationship between the fingertip portion A and the measuring portion 14, it is possible to make the force (restoring force) which is supplied from the fixing force supply portion 13 be small in comparison with the fingertip measuring unit 1. Accordingly, even if the restoring force which is supplied by the fixing force supply portion 13 is made to be smaller, it is possible to stabilize the intensity of the measured fluorescence. Furthermore, in order to be suitable in the state of stabilizing the fingertip portion A and the measuring portion 14, the length of the protruding portion of the measuring portion 14 is preferably 0.5 mm or more to 2 mm or less, and is more preferably approximately 1 mm. Since the area of the measuring face 143 is smaller than the area of an abdominal portion of the fingertip portion A, if the fingertip portion A is pressed against the measuring face 143, the measuring portion 14 is in the state of pushing up a portion which is in contact with the measuring face 143 in the fingertip portion A. Hereby, since the positional deviation of the fingertip portion A can be suppressed in comparison with the fingertip measuring unit 1, a value of the load that is supplied to the fingertip portion A may be smaller than a value (predetermined value, for example, 6N) of the load which is necessary to stabilize the intensity of the fluorescence by the fingertip measuring unit 1. Among the fingertip measuring units described later, the fingertip measuring unit where the measuring portion 14 protrudes is similar thereto.

Embodiment 3

Figure 9:
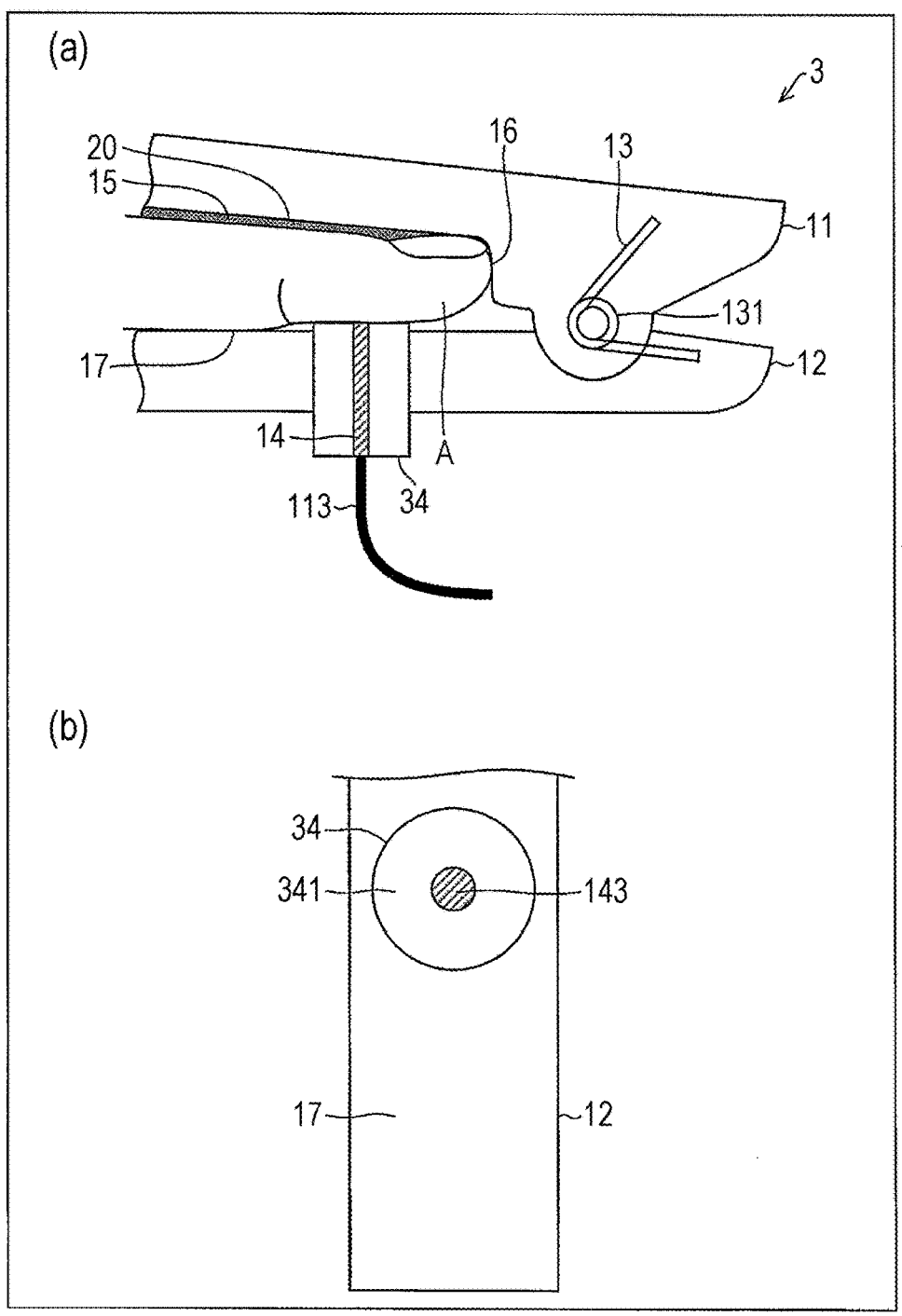
FIG. 9(a) is a sectional view illustrating a fingertip measuring unit according to Embodiment 3.
FIG. 9(b) is a schematic view illustrating a placing portion when viewed from a direction of an interposing portion.

If being described based on FIG. 9, still another embodiment of the present invention is described as follows. FIG. 9(a) is a sectional view illustrating a fingertip measuring unit 3 according to Embodiment 3, and FIG. 9(b) is a schematic view illustrating the placing portion 12 when viewed from a direction of the interposing portion 11.

As illustrated in FIG. 9(a), the fingertip measuring unit 3 according to Embodiment 3 has a configuration of forming an outer edge portion 34 (sleeve) on the periphery of the measuring portion 14 which protrudes from the placing face 17 of the placing portion 12. In Embodiment 3, the measurement attachments are realized by the measuring portion 14 and the outer edge portion 34. The outer edge portion 34 according to Embodiment 3, is a relieving member that relieves the force which is supplied to the fingertip portion A from the measuring portion 14 when the load which is capable of fixing the relative positional relationship is supplied to the fingertip portion A. As illustrated in FIG. 9(a), the outer edge portion 34 has the protruding portion of the same length (length which is from the placing face 17 to the measuring face 143 of the measuring portion 14) as the measuring portion 14. That is, the measuring face 143 is present within the plane including an outer edge contact face 341. As illustrated in FIG. 9(b), the outer edge portion 34 according to Embodiment 3 has a cylindrical shape, and has a configuration of arranging the measuring portion 14 in a space portion on an inside of the cylinder. Moreover, as illustrated in FIG. 9(b), a field that is formed by an outer periphery of the measuring portion 14 and an outer periphery of the outer edge portion 34, becomes the outer edge contact face 341 which is in contact with the finger (fingertip portion A) of the user. That is, the outer edge contact face 341 is a face which faces the interposing portion 11, and is capable of being in contact with the fingertip portion A in the outer edge portion 34.

Hereby, since the fingertip portion A is pressed against the outer edge contact face 341 of which the area is larger than that of the measuring face 143, the force which is supplied to the abdominal portion of the fingertip portion A is dispersed, in comparison with the fingertip measuring unit 2 according to Embodiment 2, and it is possible to reduce the pain which the user feels by the local pressing. Moreover, there is a merit that a measurement trace which is generated in the fingertip portion A by strongly pressing the fingertip portion A against the measuring portion 14 is not left in the fingertip measuring unit 3 according to Embodiment 3.

Furthermore, since the fingertip portion A is pressed against the outer edge contact face 341 of which the area is smaller than that of the placing face 17, when the load which is supplied to the fingertip portion A is uniform, the load pressure which is supplied to the fingertip portion A becomes large, in comparison with the fingertip measuring unit 1 according to Embodiment 1. In other words, in order to obtain the load which is capable of fixing the relative positional relationship between the fingertip portion A and the measuring portion 14, it is possible to make the force (restoring force) which is supplied from the fixing force supply portion 13 be small in comparison with the fingertip measuring unit 1. Accordingly, even if the restoring force which is supplied by the fixing force supply portion 13 is made to be smaller, it is possible to stabilize the intensity of the measured fluorescence.

In order to be suitable in the state of stabilizing the fingertip portion A and the measuring portion 14, an outer diameter of the outer edge portion 34 is preferably 1 cm or less, and is more preferably approximately 8 mm. Similarly, in order to be suitable in the state of stabilizing the fingertip portion A and the measuring portion 14, the length of the protruding portion of the measuring portion 14 and the outer edge portion 34 is preferably 0.5 mm or more to 2 mm or less, and is more preferably approximately 1 mm. Furthermore, the outer edge portion 34 according to Embodiment 3 has the cylindrical shape, but the shape of the outer edge portion 34 is not limited thereto, and for example, may be a square tube shape where the measuring portion 14 is arranged on the inside of a rectangular parallelepiped.

Moreover, since the area of the outer edge contact face 341 is smaller than the area of the abdominal portion of the fingertip portion A, if the fingertip portion A is pressed against the outer edge contact face 341, the outer edge portion 34 is in the state of pushing up a portion which is in contact with the outer edge contact face 341 in the fingertip portion A. Hereby, since the positional deviation of the fingertip portion A can be suppressed in comparison with the fingertip measuring unit 1, the value of the load that is supplied to the fingertip portion A may be smaller than the value (predetermined value, for example, 6N) of the load which is necessary to stabilize the intensity of the fluorescence by the fingertip measuring unit 1. Among the fingertip measuring units described later, the fingertip measuring unit including the outer edge portion 34 is similar thereto.

For example, as a material of the outer edge portion 34, an acrylic resin, stainless steel (SUS) or the like is used, but is not limited thereto, and is favorable if being capable of releasing the force which is supplied to the fingertip portion A from the measuring portion 14.

Embodiment 4

Figure 10:
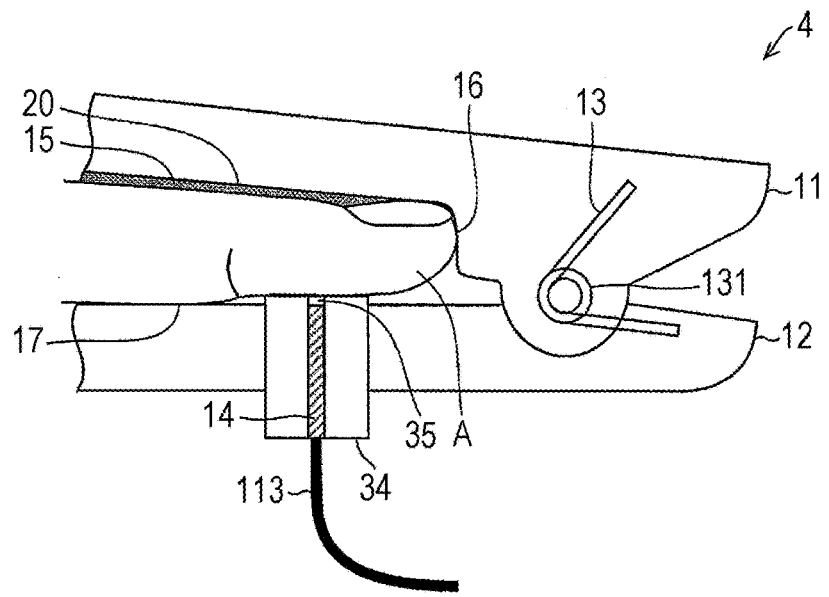
FIG. 10 is a sectional view illustrating a fingertip measuring unit according to Embodiment 4.

If being described based on FIG. 10, still another embodiment of the present invention is described as follows. FIG. 10 is a sectional view illustrating a fingertip measuring unit 4 according to Embodiment 4.

As illustrated in FIG. 10, in the fingertip measuring unit 4 according to Embodiment 4, a concave portion 35 is formed by the outer edge portion 34 and the measuring portion 14, by positioning the light-receiving face (measuring face 143) being a face that receives the fluorescence from the fingertip portion A at the position which is deeper than the outer edge contact face 341 in the measuring portion 14 having the outer edge portion 34 on the periphery thereof. Specifically, as illustrated in FIG. 10, the measuring face 143 of the measuring portion 14 which has the same height as the outer edge contact face 341 in the fingertip measuring unit 3 according to Embodiment 3, has the same height as the placing face 17 in the fingertip measuring unit 4 according to Embodiment 4. That is, the measuring face 143 is present within the plane including the placing face 17. Hereby, in the fingertip measuring unit 4 according to Embodiment 4, the concave portion 35 is formed by an internal side face of the outer edge portion 34 and the measuring face 143 of the measuring portion 14. Accordingly, when the outer edge contact face 341 is pressed against the fingertip portion A, since the measuring face 143 of the measuring portion 14 is in non-contact with the fingertip portion A, it is possible to maintain the measuring face 143 in the clean state at all times.

Furthermore, the measuring face 143 is not necessary to be present within the plane including the placing face 17, but is favorable if the position is defined so that the concave portion 35 is formed to the degree of being in non-contact with the fingertip portion A when the finger is inserted. However, if the outer edge contact face 341 and the measuring face 143 are separated too much, since the intensity of the received fluorescence is weakened, the distance between the outer edge contact face 341 and the measuring face 143, namely, the height of the concave portion 35 is preferably 0.5 mm or more to 2 mm or less, and is more preferably approximately 1 mm.

Embodiment 5

Figure 11:
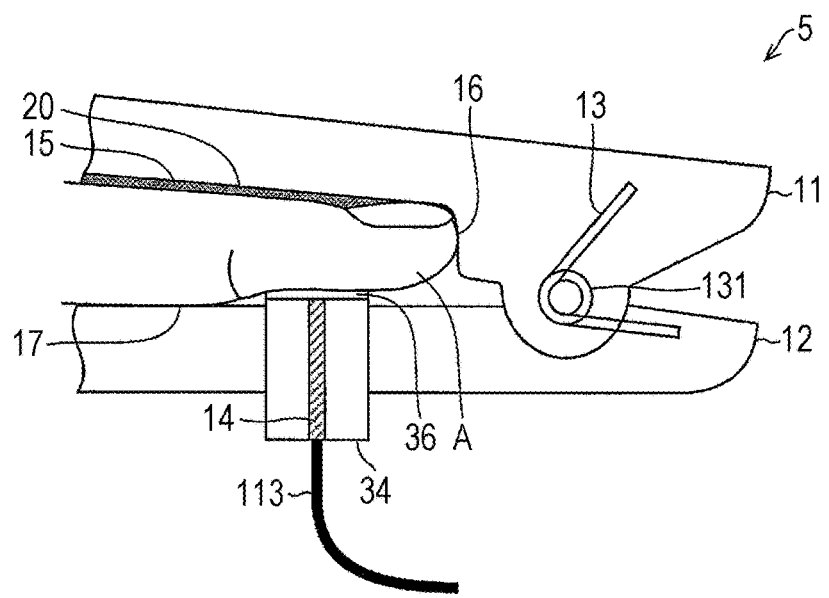
FIG. 11 is a sectional view illustrating a fingertip measuring unit according to Embodiment 5, and a modification example thereof.

If being described based on FIG. 11, still another embodiment of the present invention is described as follows. FIG. 11 is a sectional view illustrating a fingertip measuring unit 5 according to Embodiment 5.

As illustrated in FIG. 11, the fingertip measuring unit 5 according to Embodiment 5 has the configuration of forming the outer edge portion 34 on the periphery of the measuring portion 14 which protrudes from the placing face 17 of the placing portion 12, in the same manner as the fingertip measuring unit 3 according to Embodiment 3. On the other hand, a point which is different from the fingertip measuring unit 3 is that a detachable light-transmitting member 36 is arranged on the outer edge contact face 341. The light-transmitting member 36 according to Embodiment 5 has a column shape of a base area which is the same as the area of the surface including the outer edge contact face 341 and the measuring face 143 of the measuring portion 14. Moreover, in the light-transmitting member 36, a bottom face which is in contact with the outer edge contact face 341 is formed of quartz, and other portions thereof are formed of plastic. Since quartz is excellent in light-transmitting properties, even if the light-transmitting member 36 is arranged on the measuring face 143, it is possible to maintain the intensity of the excitation light that reaches the fingertip portion A from the measuring face 143, and the intensity of the fluorescence which reaches the measuring face 143 of the measuring portion 14 from the fingertip portion A.

As described above, in the fingertip measuring unit 5 according to Embodiment 5, the detachable light-transmitting member 36 is arranged on the outer edge contact face 341. Hereby, since the fingertip portion A is pressed against the light-transmitting member 36, the measuring face 143 of the measuring portion 14 is in non-contact with the fingertip portion A. Accordingly, it is possible to maintain the measuring face 143 in the clean state at all times. Moreover, since the light-transmitting member 36 is detachable, whenever the user using the fingertip measuring unit 5 is changed, it is possible to change the light-transmitting member 36, and it is possible to achieve an improvement of a sanitary side.

Furthermore, the light-transmitting member 36 according to Embodiment 5, has the column shape of the base area which is the same as the area of the surface including the outer edge contact face 341 and the measuring face 143 of the measuring portion 14, but is not limited to the configuration. The base area of the light-transmitting member 36 is favorable if the measuring face 143 of the measuring portion 14 and the outer edge contact face 341 may be in non-contact with the fingertip portion A, and is favorable if not being the same as the areas of the outer edge contact face 341 and the measuring face 143 of the measuring portion 14. Moreover, the light-transmitting member 36 is favorable if being formed into a shape such as a square pole shape other than the column shape, but in order to stably fit to the outer edge contact face 341, it is preferable that the shape of the bottom face of the light-transmitting member 36 matches with the shape of the surface including the measuring face 143 and the outer edge contact face 341.

Still more, the height of the light-transmitting member 36 (in the light-transmitting member 36, the distance which is from the face which is in contact with the fingertip portion A up to the face which is in contact with the outer edge contact face 341) is preferably 0.5 mm or more to 2 mm or less, and is more preferably approximately 1 mm, in order to maintain the intensity of the received fluorescence.

Furthermore, the light-transmitting member 36 may have a mirror face portion (not illustrated) that is capable of reflecting the fluorescence on the side face thereof. Hereby, the fluorescence which is emitted from the fingertip portion A, is reflected by the mirror face portion. Accordingly, it is possible to efficiently concentrate the fluorescence which is emitted from the fingertip portion A on the measuring face 143 of the measuring portion 14.

In addition, the light-transmitting member 36 may be arranged on the outer edge contact face 341 in the fingertip measuring unit 4 according to Embodiment 4. In this case, since the light-transmitting member 36 and the concave portion 35 are present between the fingertip portion A and the measuring face 143 of the measuring portion 14, the sum of the heights of the light-transmitting member 36 and the concave portion 35 (that is, the distance of the light-transmitting member 36 that is from the surface which may be in contact with the fingertip portion A up to the measuring face 143 of the measuring portion 14) is preferably 0.5 mm or more to 2 mm or less.

Embodiment 6

Figure 12:
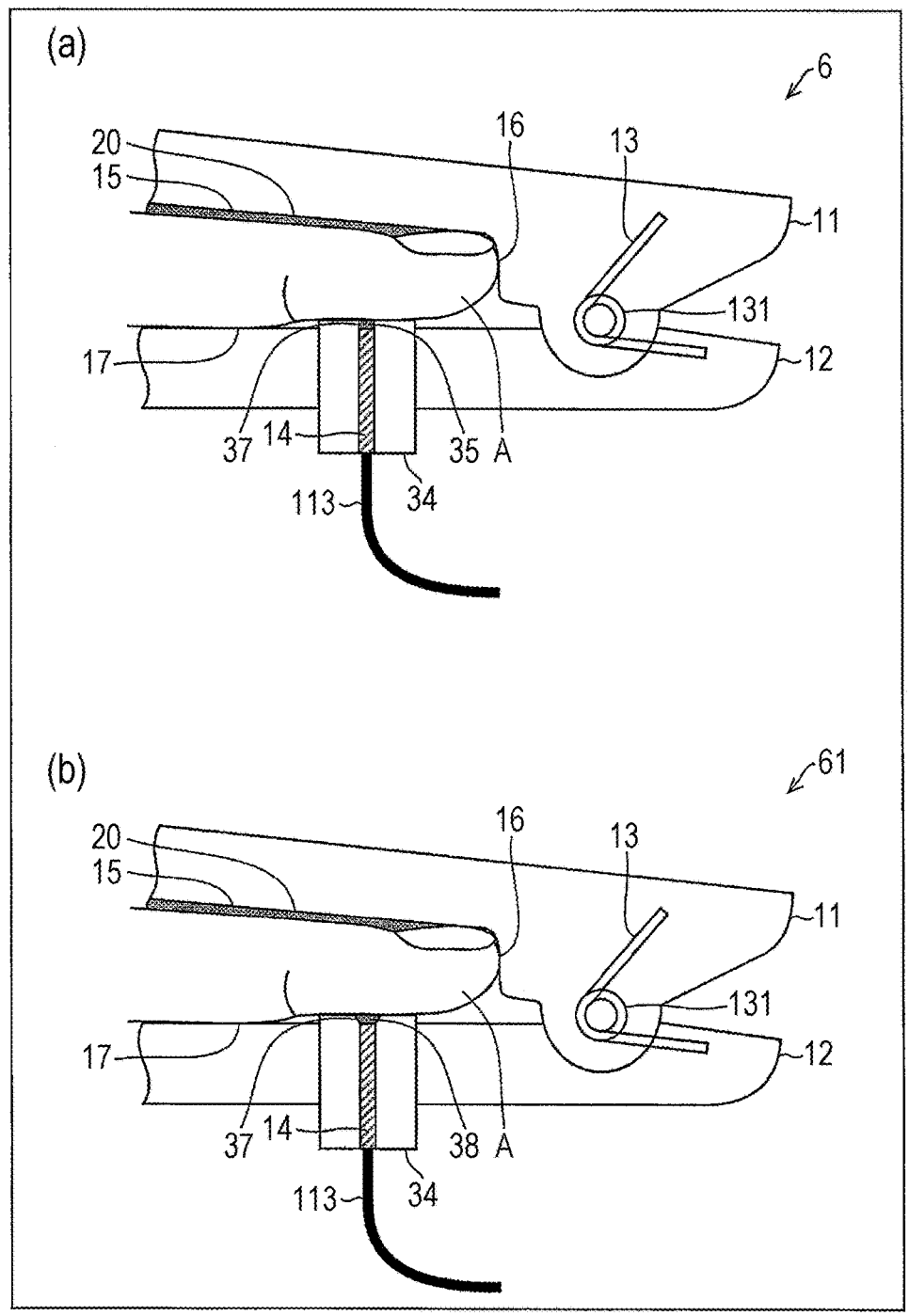
FIG. 12(a) and FIG. 12(b) are sectional views illustrating a fingertip measuring unit according to Embodiment 6.

If being described based on FIG. 12, still another embodiment of the present invention is described as follows. FIG. 12 is a sectional view illustrating a fingertip measuring unit 6 according to Embodiment 6, and a fingertip measuring unit 61 being a modification example of the fingertip measuring unit 6.

As illustrated in FIG. 12(*a*), in the fingertip measuring unit 6 according to Embodiment 6, the concave portion 35 is formed by the outer edge portion 34 and the measuring portion 14, by positioning the measuring face 143 being a face that receives the fluorescence from the fingertip portion A at the position which is deeper than the outer edge contact face 341, in the same manner as the fingertip measuring unit 4 according to Embodiment 4. Therefore, the point that is different from the fingertip measuring unit 4 is that a mirror face portion 37 which reflects the incident fluorescence is included on the side face within the concave portion 35. The mirror face portion 37 according to Embodiment 6, is formed by depositing aluminum on the side face of the concave portion 35.

In the fingertip measuring unit 4, since the fingertip portion A and the measuring face 143 of the measuring portion 14 are separated, the intensity of the fluorescence that reaches the measuring face 143 may be weakened, by absorbing the fluorescence which is emitted from the fingertip portion A on the side face of the concave portion 35. On the other hand, in the fingertip measuring unit 6 according to Embodiment 6, since the mirror face portion 37 is included on the side face within the concave portion 35, the fluorescence is not absorbed on the side face of the concave portion 35, by that the fluorescence is reflected by the mirror face portion 37. Hereby, in the state of suppressing that the intensity of the fluorescence which is emitted from the fingertip portion A is weakened, since the fluorescence may be incident to the measuring face 143, it is possible to efficiently concentrate the fluorescence. That is, it is possible to suppress the decrease of the intensity of the fluorescence by forming the concave portion 35, and it is possible to maintain the intensity of the measured fluorescence.

As illustrated in FIG. 12(*b*), the fingertip measuring unit according to Embodiment 6 may be a fingertip measuring unit 61 including the mirror face portion 37 on a side face within a concave portion 38 of a tapered shape. By making the concave portion into the concave portion 38 of the tapered shape (sectional shape of the concave portion is open into a fan shape), since the fluorescence may be more efficiently concentrated on the measuring face 143 of the measuring portion 14, it is possible to make the intensity of the fluorescence be strong in comparison with the fingertip measuring unit 6.

Moreover, the mirror face portion 37 according to Embodiment 6, is formed by depositing aluminum on the side face within the concave portion 35 and the concave portion 38, but the mirror face portion 37 is favorable if being capable of reflecting the fluorescence, and is not limited to aluminum.

Still more, the light-transmitting member 36 described in Embodiment 5, may be arranged on the outer edge contact face 341 of the outer edge portion 34 which is included in the fingertip measuring units 6 and 61 according to Embodiment 6.

Embodiment 7

Figure 13:
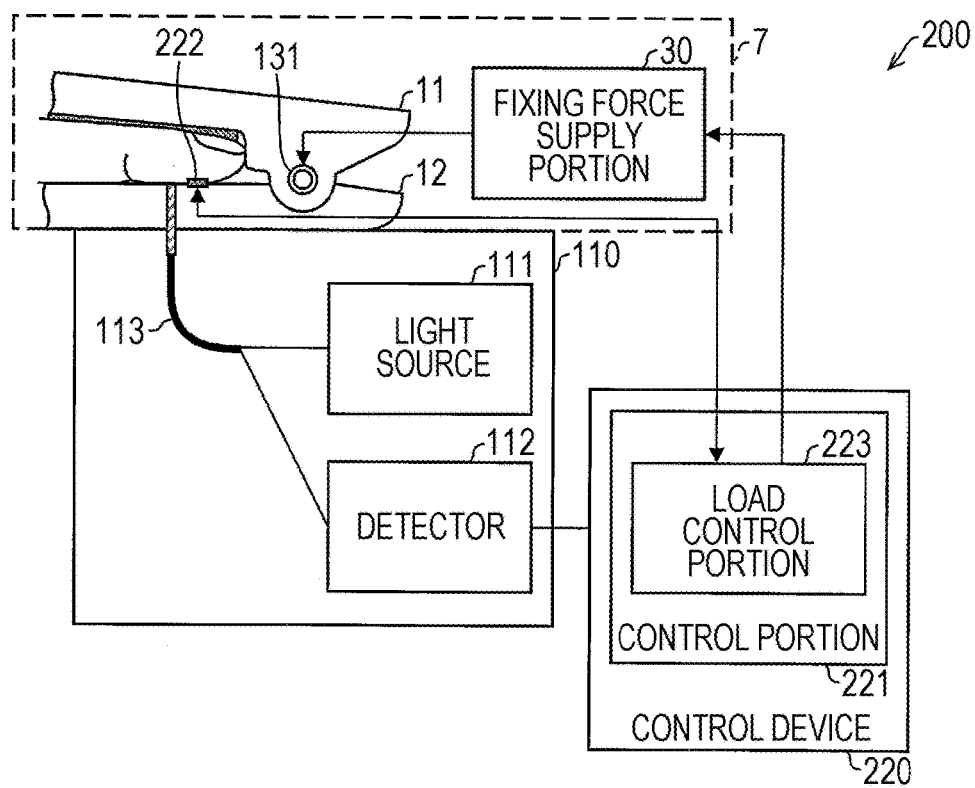
FIG. 13 is a diagram illustrating a configuration of a fingertip measuring device according to Embodiment 7.

If being described based on FIG. 13, still another embodiment of the present invention is described as follows. FIG. 13 is a diagram illustrating a configuration of a fingertip measuring device 200 according to Embodiment 7. As illustrated in FIG. 13, the fingertip measuring device 200 is configured to include a fingertip measuring unit 7, a measuring member arrangement portion 110, and a control device 220. Here, since the measuring member arrangement portion 110 is similar to the measuring member arrangement portion 110 described in Embodiment 1, the description will be omitted.

(Fingertip Measuring Unit 7)

The fingertip measuring unit 7 according to Embodiment 7, further includes a load sensor 222 (fixing force sensor) that measures the value of the load which is applied to the fingertip portion A of the inserted finger. Moreover, the fingertip measuring unit 7 is configured to include a fixing force supply portion 30 which is controlled by a load control portion 223 so that the load becomes the predetermined value or more depending on a measurement result by the load sensor 222, instead of the fixing force supply portion 13 which is included in the fingertip measuring units 1 to 6.

(Load Sensor 222)

The load sensor 222 is a sensor that measures the value of the load which is applied to the fingertip portion A of the inserted finger through the interposing portion 11 by the fixing force supply portion 30. Specifically, the load sensor 222 measures the load which is applied to the fingertip portion A through the interposing portion 11 by the fixing force supply portion 30, and outputs the measurement result to the load control portion 223. For example, the load sensor 222 starts the measurement of the load by receiving an instruction (measurement start instruction) for measuring the value of the load which is supplied to the fingertip portion A from the interposing portion 11, from the load control portion 223. Therefore, the load sensor 222 continuously measures the time-dependent change of the load which is applied to the fingertip portion A through the interposing portion 11 by the fixing force supply portion 30, and continuously outputs the measurement result to the load control portion 223. Furthermore, the details of the load control portion 223 will be described later.

For example, the load sensor 222 has a sheet shape, and is attached to a spot (for example, the buffering portion 15, the placing face 17, the outer edge contact face 341 or the like) at which the fingertip portion A touches in the fingertip measuring unit 7. For example, in FIG. 13, the load sensor 222 is arranged in the vicinity of the measuring portion 14 of the placing face 17. However, if the load which is supplied to the fingertip portion A may be accurately measured, the shape and the arrangement spot of the load sensor 222 are not limited.

(Fixing Force Supply Portion 30)

The fixing force supply portion 30 is a drive device which supplies the rotating force to the interposing portion 11, so that the interposing portion 11 is rotated in the direction of approaching the placing portion 12 by using the coupling portion 131 as a rotation axis, and for example, is a motor. Specifically, if a fix instruction for applying a predetermined load (for example, 6N) to the fingertip portion A is supplied from the load control portion 223, the fixing force supply portion 30 is driven so that the load which is indicated by the fix instruction is applied to the inserted fingertip portion A through the interposing portion 11. For example, by driving the fixing force supply portion 30, the force in the direction of the placing portion 12 is supplied to the interposing portion 11. Hereby, the interposing portion 11 is moved toward the direction of the placing portion 12, and the fingertip portion A which is inserted into the fingertip measuring unit 7 is interposed by the interposing portion 11 so as to be pressed against the placing portion 12, and the predetermined load is applied to the interposed fingertip portion A.

In FIG. 13, the fixing force supply portion 30 is illustrated on an outside of the interposing portion 11 and the placing portion 12 in consideration of viewability of the drawing, but actually, the fixing force supply portion 30 is arranged in the vicinity of the coupling portion 131.

Moreover, the fingertip measuring unit 7 according to Embodiment 7 is configured to be capable of detecting that the finger of the user is inserted. Therefore, the insertion information indicating that the finger is inserted when the finger of the user is inserted, is output to the load control portion 223.

Here, since other configurations of the fingertip measuring unit 7 are similar to any of the fingertip measuring units 1 to 6 described in Embodiments 1 to 6, the description will be omitted.

(Control Device 220)

The control device 220 of the fingertip measuring device 200 according to Embodiment 7, includes a control portion 221. Here, since other configurations thereof are similar to the control device 120 described in Embodiment 1, the description will be omitted.

(Control Portion 221)

The control portion 221 controls the respective portions of the fingertip measuring device 200. The control portion 221 is configured to include the load control portion 223 (fixing force control portion).

(Load Control Portion 223)

The load control portion 223 controls the fixing force supply portion 30, so that the load which is applied to the fingertip portion A of the inserted finger becomes the predetermined value depending on the measurement result by the load sensor 222. Specifically, if the insertion information is supplied from the fingertip measuring unit 7, the load control portion 223 starts the control of a fixing force supply portion 30. More specifically, if the insertion information is supplied, the load control portion 223 outputs the fix instruction for applying the predetermined load (for example, 6N) to the fingertip portion A to the fixing force supply portion 30. For example, the fixing force supply portion 30 of the fingertip measuring unit 7 supplies the force in the direction of the placing portion 12 to the interposing portion 11 of the fingertip measuring unit 7. Hereby, the interposing portion 11 is moved toward the direction of the placing portion 12, and the fingertip portion A which is inserted into the fingertip measuring unit 7 is interposed by the interposing portion 11 so as to be pressed against the placing portion 12, and the predetermined load is applied to the interposed fingertip portion A.

Moreover, if the insertion information is supplied from the fingertip measuring unit 7, the load control portion 223 outputs a measurement start instruction to the load sensor 222. Therefore, when the measurement result which is output from the load sensor 222 is less than the predetermined value, the load which is supplied to the fingertip portion A is made so as to be predetermined value or more, by controlling the fixing force supply portion 30. For example, the load control portion 223 applies the instruction for increasing the force which is supplied to the interposing portion, to the fixing force supply portion 30, and the load which is supplied to the fingertip portion A through the interposing portion 11, is made so as to be predetermined value or more.

Effects of Invention According to Embodiment 7

As described above, the fingertip measuring device 200 according to Embodiment 7, is configured to include the load sensor 222 that measures the value of the load which is applied to the fingertip portion A of the inserted finger through the interposing portion 11 by the fixing force supply portion 30, and the load control portion 223 that controls the load which is applied to the fingertip portion A through the interposing portion 11 by the fixing force supply portion 30 so as to be the predetermined value or more, depending on the measurement result by the load sensor 222. Hereby, only by setting in advance the predetermined value as a value (for example, 6N) such that the time-dependent change of the intensity of the fluorescence does not occur, it is possible to stabilize the intensity of the fluorescence.

Modification Example 1

Figure 14:
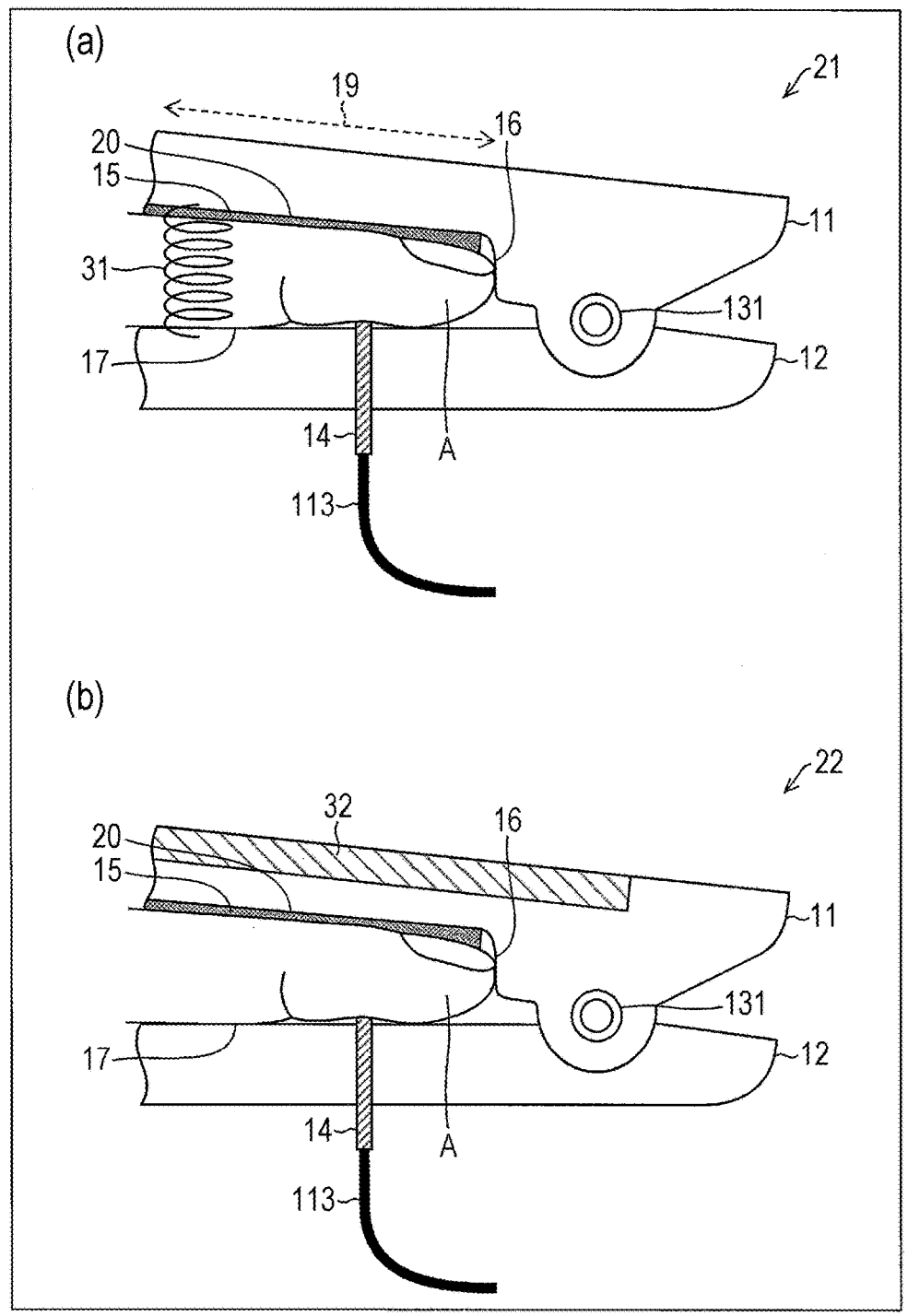
FIG. 14(a) and FIG. 14(b) are sectional views illustrating a modification example of the fingertip measuring unit.

If being described based on FIG. 14, Modification Example 1 which is common to Embodiments 1 to 6 of the present invention is described as follows. FIG. 14 is a sectional view illustrating a modification example of the fingertip measuring unit. Furthermore, FIG. 14 is described as a modification example of Embodiment 2, but Modification Example 1 may be applied to Embodiments 1 to 6 of the present invention.

The fingertip measuring units 1 to 6 described in Embodiments 1 to 6, have the fixing force supply portion 13 being the spring type hinge. However, the fixing force supply portion is favorable if the load which is capable of fixing the relative positional relationship between the fingertip portion A and the measuring portion 14, may be supplied to the fingertip portion A through the interposing portion 11, and is not limited the spring type hinge.

For example, as illustrated in FIG. 14(a), the fingertip measuring unit may be a fingertip measuring unit 21 including the fixing force supply portion 31 which is the spring so as to connect the pinch portion 19 of the interposing portion 11 to the placing portion 12. The fixing force supply portion 31 is extended by inserting the finger into the fingertip measuring unit 21, and the restoring force which tries to return to an original state is generated at the same time. By that the restoring force as load is transmitted to the fingertip portion A from the pinch portion 19, the relative positional relationship between the fingertip portion A and the measuring portion 14 is fixed. In FIG. 14(a), for simplification of the drawing, the fingertip measuring unit 21 and the fixing force supply portion 31 are displayed by being superposed, but actually, the fixing force supply portion 31 is arranged so as to connect the pinch portion 19 of the interposing portion 11 to the placing portion 12 in two places of a back side (back side of the finger) of FIG. 14(a) and a front side (front side of the finger) of FIG. 14(a). That is, the two fixing force supply portions 31 are arranged by being separated in a width direction (in the placing face 17, the direction which is substantially perpendicular to the insertion direction of the finger) of the interposing portion 11 and the placing portion 12, to the degree which is capable of inserting the finger into the placing portion 12. The strength, the number, and the arrangement of the fixing force supply portion 31 are favorable if being determined so that the relative positional relationship between the fingertip portion A and the measuring portion 14 is fixed.

As illustrated in FIG. 14(b), the fingertip measuring unit may be a fingertip measuring unit 22 including a fixing force supply portion 32 as a load member in which a portion of the interposing portion 11 is made up of a metal material having heavy specific gravity. Since the fixing force supply portion 32 is the metal of heavy specific gravity, it is possible to supply the pressing force of pressing the fingertip portion A by the self-weight of the fixing force supply portion 32, to the interposing portion 11. By supplying the pressing force as a load to the fingertip portion A from the interposing portion 11, it is possible to fix the fingertip portion A and the measuring portion 14. As a fixing force supply portion 32 (load member), iron, stainless steel (SUS) or the like may be used. Moreover, the fixing force supply portion 32 may be independently arranged on the interposing portion 11.

Modification Example 2

Figure 15:
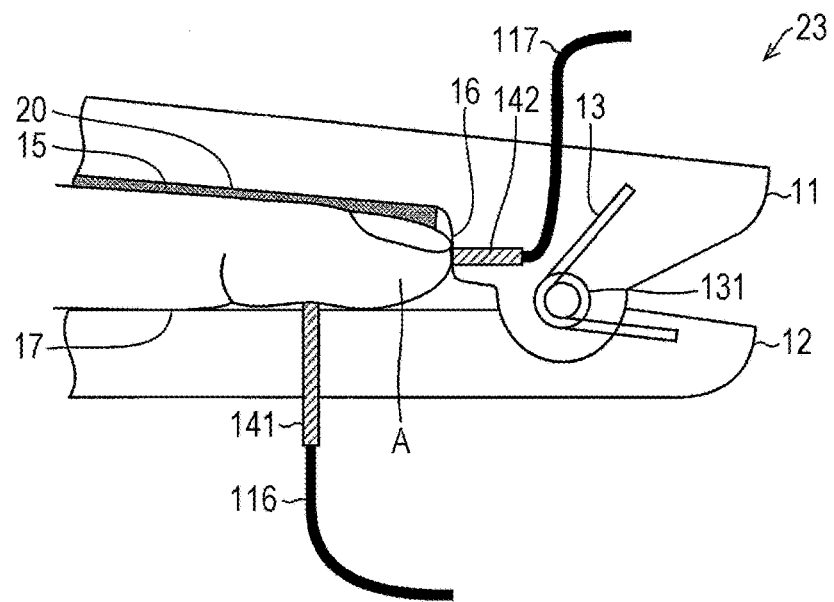
FIG. 15 is a sectional view illustrating another modification example of the fingertip measuring unit.

If being described based on FIG. 15, Modification Example 2 which is common to Embodiments 1 to 7 of the present invention is described as follows. FIG. 15 is a sectional view illustrating a modification example of the fingertip measuring unit. Furthermore, FIG. 15 is described as a modification example of Embodiment 2, but Modification Example 2 may be applied to Embodiments 1 to 7 of the present invention, and Modification Example 1.

In the fingertip measuring units described in Embodiments 1 to 7, the measuring portion 14 is a portion where the functions of the emitting portion which emits the excitation light and the light-receiving portion which receives the fluorescence are integrated. However, the measuring portion is not limited to the configuration. For example, the measuring probe may be configured by using a fiber for emission 116, and a fiber for incidence 117, instead of the measuring probe 113 (see FIG. 4). Here, since the fiber for emission 116, and the fiber for incidence 117 have the functions which are respectively similar to the fiber for emission 115, and the fiber for incidence 114, the description will be omitted.

In this case, as illustrated in FIG. 15, the measuring portion of a fingertip measuring unit 23 is configured by a light-receiving portion 141 which is an end portion of the fiber for emission 116, and receives the fluorescence, and an emitting portion 142 which is an end portion of the fiber for incidence 117, and emits the excitation light. That is, the measuring portion according to Modification Example 2 has a configuration in which the light-receiving portion 141 and the emitting portion 142 are individual.

The light-receiving portion 141 according to Modification Example 2 is arranged in the placing portion 12, in the same manner as the measuring portions 14 of Embodiments 1 to 7. Meanwhile, the emitting portion 142 according to Modification Example 2 is arranged in the positioning portion 16 of the interposing portion 11. The positions are not limited thereto, and may be respectively arranged at a position where the emitting portion 142 is capable of emitting the excitation light to the fingertip portion A, and a position where the light-receiving portion 141 is capable of receiving the fluorescence which is emitted from the fingertip portion A.

Modification Example 3

Figure 16:
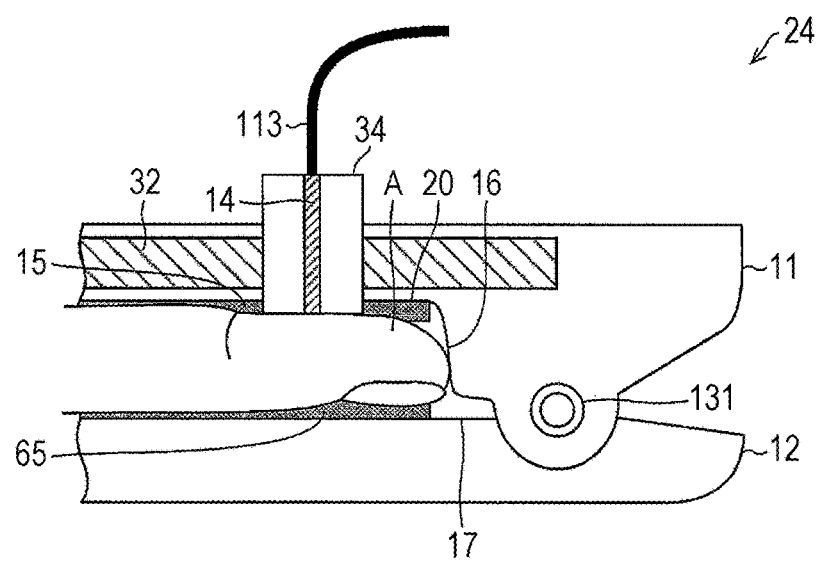
FIG. 16 is a sectional view illustrating still another modification example of the fingertip measuring unit.

If being described based on FIG. 16, Modification Example 3 which is common to Embodiments 1 to 7 of the present invention is described as follows. FIG. 16 is a sectional view illustrating a modification example of the fingertip measuring unit. Furthermore, FIG. 16 is described as a modification example of Embodiment 3, but Modification Example 3 may be applied to Embodiments 1 to 7 of the present invention, and Modification Example 1.

The fingertip measuring units described in Embodiments 1 to 7 are configured by arranging the measuring portion 14 in the placing portion 12. However, the member in which the measuring portion 14 is arranged is not limited to the placing portion 12. For example, as illustrated in FIG. 16, the measuring portion 14 may be arranged in the interposing portion 11. Moreover, when the measuring portion 14 is arranged in the interposing portion 11, a buffering portion 65 may be included on the placing face 17. Hereby, it is possible to prevent the deviation of the relative positional relationship between the fingertip portion A and the measuring portion 14, and it is possible to reduce the pain that the user feels.

Moreover, a fingertip measuring unit 24 illustrated in FIG. 16, is configured to include the fixing force supply portion 32 being the load member which is made up of the metal material having heavy specific gravity, but is not limited to the configuration. The fixing force supply portion of Modification Example 3 may be the fixing force supply portion 13 which is the spring type hinge, or may be the fixing force supply portion 31 which is the spring, as described in Embodiments 1 to 7. In the case of Modification Example 3, the outer edge portion 34 may be made up of the metal material having heavy specific gravity, instead of the fixing force supply portion 32.

Furthermore, the fingertip measuring unit 24 illustrated in FIG. 16, is configured to include the buffering portion 15 on the facing face 20, but the fingertip measuring unit according to Modification Example 3 is not limited to the configuration illustrated in FIG. 16. For example, the configuration may be a configuration in which the buffering portion 15 is not included, and the measuring portion 14 and the outer edge portion 34 protrude from the facing portion 15 and the outer edge portion 34 are not included, and the measuring portion 14 protrudes from the facing face 20.

The present invention is not limited to the each of embodiments described above, but may be modified within the scope which is illustrated in the claims, and an embodiment that is obtained by appropriately combining technical methods which are respectively disclosed in the different embodiments is also included in the technical scope of the present invention. Furthermore, by combining the technical methods which are respectively disclosed in each of embodiments, it is possible to form a new technical feature.

INDUSTRIAL APPLICABILITY

The present invention may be used in the measuring device that measures the amount of the fluorescent material, based on the intensity of the fluorescence which is generated from the fluorescent material within the living body, and is particularly suitable for the measuring device that monitors the AGEs within the living body.

REFERENCE SIGNS LIST

1 FINGERTIP MEASURING UNIT
2 FINGERTIP MEASURING UNIT
3 FINGERTIP MEASURING UNIT
4 FINGERTIP MEASURING UNIT
5 FINGERTIP MEASURING UNIT
6 FINGERTIP MEASURING UNIT
7 FINGERTIP MEASURING UNIT
21 FINGERTIP MEASURING UNIT
22 FINGERTIP MEASURING UNIT
23 FINGERTIP MEASURING UNIT
24 FINGERTIP MEASURING UNIT
61 FINGERTIP MEASURING UNIT
11 INTERPOSING PORTION
12 PLACING PORTION
13 FIXING FORCE SUPPLY PORTION
14 MEASURING PORTION (EMITTING PORTION, LIGHT-RECEIVING PORTION)
17 PLACING FACE (FACING FACE)
20 FACING FACE
30 FIXING FORCE SUPPLY PORTION
31 FIXING FORCE SUPPLY PORTION
32 FIXING FORCE SUPPLY PORTION
34 OUTER EDGE PORTION
35 CONCAVE PORTION
36 LIGHT-TRANSMITTING MEMBER
37 MIRROR FACE PORTION
38 CONCAVE PORTION
100 FINGERTIP MEASURING DEVICE (MEASURING DEVICE)
141 LIGHT-RECEIVING PORTION
142 EMITTING PORTION
143 MEASURING FACE (LIGHT-RECEIVING FACE)
200 FINGERTIP MEASURING DEVICE (MEASURING DEVICE)
222 LOAD SENSOR (FIXING FORCE SENSOR)
223 LOAD CONTROL PORTION (FIXING FORCE CONTROL PORTION)
341 OUTER EDGE CONTACT FACE
A FINGERTIP PORTION (MEASUREMENT TARGET REGION, FINGERTIP)

The invention claimed is:

1. A measuring device measuring an amount of a fluorescent material, based on an intensity of fluorescence that is generated from the fluorescent material within a living body excited by excitation light with which a measurement target region of the living body is irradiated, the device comprising:
a placing portion where the measurement target region is placed;
an interposing portion that faces the placing portion, the measurement target region being interposed between the placing portion and the interposing portion;
an emitting portion that is arranged in one of the placing portion and the interposing portion, and emits the excitation light;
a light-receiving portion that is arranged in one of the placing portion and the interposing portion, and receives the fluorescence; and
a fixing force supply portion that supplies, to the measurement target region through the interposing portion, force which is capable of fixing a relative positional relationship between the measurement target region and the light-receiving portion.

2. The measuring device according to claim 1, wherein the placing portion and the interposing portion have facing faces which face each other in a state of interposing the measurement target region therebetween, and
the light-receiving portion protrudes from the facing face of the placing portion or of the interposing portion.

3. The measuring device according to claim 2, further comprising:
an outer edge portion that is formed on a periphery of the light-receiving portion,
wherein the outer edge portion has an outer edge contact face which contacts with the measurement target region.

4. The measuring device according to claim 3,
wherein the light-receiving portion has a light-receiving face which receives the fluorescence, and
a concave portion is formed by positioning the light-receiving face at a position which is deeper than the outer edge contact face.

5. The measuring device according to claim 4, further comprising:
a mirror face portion provided on a side face within the concave portion, wherein the mirror face portion reflects portions of the fluorescence which are incident on the mirror face portion.

6. The measuring device according to claim 3,
wherein a detachable light-transmitting member is arranged on the outer edge contact face.

7. The measuring device according to claim 4, wherein a detachable light-transmitting member is arranged on the outer edge contact face.

8. The measuring device according to claim 1, further comprising:
a fixing force sensor that measures a value of force which is applied by the fixing force supply portion; and
a fixing force control portion that controls the fixing force supply portion such that the force which is applied by the fixing force supply portion is a predetermined value or more, depending on a measurement result by the fixing force sensor.

9. The measuring device according to claim 1, wherein the measurement target region is a fingertip.

* * * * *